US010885400B2

(12) United States Patent
Zhao et al.

(10) Patent No.: US 10,885,400 B2
(45) Date of Patent: Jan. 5, 2021

(54) CLASSIFICATION BASED ON ANNOTATION INFORMATION

(71) Applicant: General Electric Company, Schenectady, NY (US)

(72) Inventors: Qian Zhao, Dublin, CA (US); Min Zhang, San Ramon, CA (US); Gopal Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 96 days.

(21) Appl. No.: 16/143,703

(22) Filed: Sep. 27, 2018

(65) Prior Publication Data

US 2020/0012904 A1 Jan. 9, 2020

Related U.S. Application Data

(60) Provisional application No. 62/693,772, filed on Jul. 3, 2018.

(51) Int. Cl.
*G06K 9/00* (2006.01)
*G06K 9/66* (2006.01)
*G06K 9/32* (2006.01)
*G06N 3/08* (2006.01)

(52) U.S. Cl.
CPC ........... *G06K 9/66* (2013.01); *G06K 9/00671* (2013.01); *G06K 9/3241* (2013.01); *G06N 3/08* (2013.01)

(58) Field of Classification Search
CPC .... G06K 9/66; G06K 9/00671; G06K 9/3241; G06N 3/08
See application file for complete search history.

(56) References Cited

U.S. PATENT DOCUMENTS

| 9,916,522 B2 | 3/2018 | Ros Sanchez et al. |
| 10,140,544 B1 | 11/2018 | Zhao et al. |
| 10,185,891 B1 | 1/2019 | Martin |
| 2017/0169567 A1* | 6/2017 | Chefd'hotel ......... G06N 3/0454 |

(Continued)

OTHER PUBLICATIONS

Li et al. "Thoracic Disease Identification and Localization with Limited Supervision," arXiv:1711.06373v4 [cs.CV], Mar. 28, 2018, 12 pages.

(Continued)

*Primary Examiner* — Ping Y Hsieh
(74) *Attorney, Agent, or Firm* — Amin, Turocy & Watson, LLP

(57) ABSTRACT

Systems and techniques for classification based on annotation information are presented. In one example, a system trains a convolutional neural network based on training data and a plurality of images. The plurality of images is associated with a plurality of masks, a plurality of image level labels, and/or a bounding box. The system also generates a first loss function based on the plurality of masks, a second loss function based on the plurality of image level labels, and a third loss function based on the bounding box. Furthermore, the system generates a fourth loss function based on the first loss function, the second loss function and the third loss function, where the fourth loss function is iteratively back propagated to tune parameters of the convolutional neural network. The system also predicts a classification label for an input image based on the convolutional neural network.

20 Claims, 11 Drawing Sheets

(56) References Cited

U.S. PATENT DOCUMENTS

| | | |
|---|---|---|
| 2017/0278289 A1 | 9/2017 | Marino et al. |
| 2018/0060722 A1 | 3/2018 | Hwang et al. |
| 2018/0075343 A1 | 3/2018 | van den Oord et al. |
| 2018/0082172 A1 | 3/2018 | Patel et al. |
| 2018/0101957 A1 | 4/2018 | Talathi |
| 2018/0144193 A1 | 5/2018 | Tang et al. |
| 2018/0260957 A1 | 9/2018 | Yang et al. |
| 2018/0268737 A1 | 9/2018 | Gamavi et al. |
| 2019/0043003 A1 | 2/2019 | Fisher et al. |
| 2019/0050981 A1* | 2/2019 | Song ................. G06T 11/20 |
| 2019/0073569 A1* | 3/2019 | Ben-Ari ............. A61B 6/5217 |
| 2019/0122075 A1 | 4/2019 | Zhang et al. |
| 2019/0164290 A1* | 5/2019 | Wang ................. G06T 7/10 |
| 2019/0205606 A1 | 7/2019 | Zhao et al. |
| 2019/0251398 A1 | 8/2019 | Godwin, IV et al. |
| 2019/0266418 A1 | 8/2019 | Xu et al. |
| 2019/0286880 A1* | 9/2019 | Jackson ............. G16H 50/20 |
| 2019/0304092 A1* | 10/2019 | Akselrod-Ballin ...... G06N 3/08 |
| 2019/0313963 A1 | 10/2019 | Hillen |
| 2019/0318822 A1* | 10/2019 | Zhang ............... G06K 9/6257 |
| 2020/0012895 A1 | 1/2020 | Zhao et al. |
| 2020/0012904 A1 | 1/2020 | Zhao et al. |

OTHER PUBLICATIONS

Kaiming He et al: "Mask R-CNN", Jan. 24, 2018 (Jan. 24, 2018), XP055621354, Retrieved from the Internet: URL: https://arxiv.org/pdf/1703.06870.pdf [retrieved on Sep. 11, 2019]; abstract, p. 2961-p. 2964, figures 1-4.

PCT application PCT/US2019/039718 filed Jun. 28, 2019; International Search Report-Written Opinion dated Sep. 23, 2019, 15 pages.

Shaoqing Ren et al: "Faster R-CNN: Towards Real-Time Object Detection with Region Proposal Networks", Advances in Neural Information Processing Systems (NIPS 2015), Dec. 7, 2015 (Dec. 7, 2015), XP055488147, abstract p. 1-p. 5, figure 1.

Zichen Zhang et al: "End-to-end detection-segmentation network with ROI convolution", arxiv.org, Cornell University Library, 201 Olin Library Cornell University Ithace, NY 14853, Jan. 9, 2018 (Jan. 9, 2018), XP081204838, abstract; p. 1-p. 4, figures 1,3.

International Search Report/Written Opinion dated Sep. 23, 2019; pet application PCT/US2019/039711 filed Jun. 28, 2019.

Non-Final Office Action received for U.S. Appl. No. 16/046,084 dated Jan. 21, 2020, 60 pages.

Non-Final Office Action received for U.S. Appl. No. 16/054,373 dated Mar. 25, 2020, 46 pages.

Fu et al., Joint Optic Disc and Cup Segmentation Based on Multi-Label Deep Network and Polar Transformation, Jan. 9, 2018 (first public dissemination), publish Jul. 2018 [retrivd Mar. 18, 2020], IEEE Trans on Med Imag, vol. 37, Iss: 7, pp. 1597-1605. https://ieeexplore.ieee.org/abstract/document/8252743 (Year: 2018).

Non-Final Office Action received for U.S. Appl. No. 16/058,984 dated Jan. 17, 2020, 49 pages.

Mehta et al., DeepSolarEye: Power Loss Prediction and Weakly Supervised Soiling Localization via Fully convolutional Networks for Solar Panels, Mar. 12-15, 2018 [retri Sep. 4, 2020], 2018 IEEE Winter Conf on App of Comp Vision,pp. 333-342. https://ieeexplore.ieee.org/abstract/document/8354147 (Year: 2018).

Sladojevic et al., Deep Neural Networks Based Recognition of Plant Diseases by Leaf Image Classification, Jun, 22, 2016 [retrieved Sep. 4, 2020], Computational Intelligence and Neuroscience, vol. 2016, pp. 1-11. Retrieved: https://www.hindawi.com/journals/cin/2016/3289801 / (Year: 2016).

Final Office Action received for U.S. Appl. No. 16/054,373 dated Sep. 10, 2020, 79 pages.

* cited by examiner

CLASSIFICATION BASED ON ANNOTATION INFORMATION

RELATED APPLICATION

This application claims priority to U.S. Provisional Application No. 62/693,772, filed Jul. 3, 2018, and entitled "CLASSIFICATION AND/OR LOCALIZATION BASED ON ANNOTATION INFORMATION", the entirety of which is incorporated herein by reference.

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance imaging analysis. In an example, region-of-interest based deep neural networks can be employed to localize a feature in a digital image. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a training component, a first loss function component, a second loss function component, a third loss function component, a fourth loss function component, and a classification component. The training component trains a convolutional neural network based on training data and a plurality of images. The training data is associated with a plurality of patients from at least one imaging device. The plurality of images is associated with a plurality of masks from a plurality of objects, a plurality of image level labels for the plurality of images, and/or a bounding box that links a region of interest to a class label. The first loss function component generates a first loss function based on the plurality of masks. The second loss function component generates a second loss function based on the plurality of image level labels for the plurality of images. The third loss function component generates a third loss function based on the bounding box that links a region of interest to the class label. The fourth loss function component generates a fourth loss function based on the first loss function, the second loss function and the third loss function, where the fourth loss function is iteratively back propagated to tune parameters of the convolutional neural network. The classification component that predicts a classification label for an input image based on the convolutional neural network.

According to another embodiment, a method is provided. The method comprises receiving a plurality of images associated with a plurality of patients from at least one imaging device. The method also comprises receiving a plurality of masks from a plurality of objects, wherein each image comprises at least one mask associating an object of interest with a corresponding class label, at least one image level label for the image, and/or a bounding box that links the object of interest to the corresponding class label. Furthermore, the method comprises training a convolutional neural network based on the plurality of images, the plurality of masks, the bounding box and/or the at least one image level label, where the convolutional neural network comprises a pretrained classifier network that outputs convolutional feature maps, and a classification/localization network that outputs corresponding localization maps. The method also comprises generating a first loss function based on the plurality of masks. The method also comprises generating a second loss function based on the at least one image level label for the image. The method also comprises generating a third loss function based on the bounding box that links the object of interest to the corresponding class label. The method also comprises generating a fourth loss function based on the first loss function, the second loss function and the third loss function. Additionally, the method comprises iteratively back propagating the fourth loss function to tune parameters of the convolutional neural network. The method also comprises predicting a classification label for an input image based on the convolutional neural network.

According to yet another embodiment, a computer readable storage device is provided. The computer readable storage device comprises instructions that, in response to execution, cause a system comprising a processor to perform operations, comprising receiving a plurality of images associated with a plurality of patients from at least one imaging device. The processor also performs operations, comprising receiving a plurality of masks from a plurality of objects, where each image comprises at least one mask associating an object of interest with a corresponding class label, at least one image level label for the image, and/or a bounding box that links the object of interest to the corresponding class label. The processor also performs operations, comprising training a convolutional neural network based on the plurality of images, the plurality of masks, the bounding box and/or the at least one image level label, where the convolutional neural network comprises a pretrained classifier network that outputs convolutional feature maps, and a classification/localization network that outputs corresponding localization maps. Furthermore, the processor performs operations, comprising generating a first loss function based on the plurality of masks. Furthermore, the processor performs operations, comprising generating a second loss function based on the at least one image level label for the image. Furthermore, the processor performs operations, comprising generating a third loss function based on the bounding box that links the object of interest to the corresponding class label. Furthermore, the processor performs operations, comprising generating a fourth loss function based on the first loss function, the second loss function and the third loss function. The processor also performs operations, comprising iteratively back propagating the fourth loss function to tune parameters of the convolutional neural network. The processor also performs operations, comprising predicting a classification label for an input image based on the convolutional neural network.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
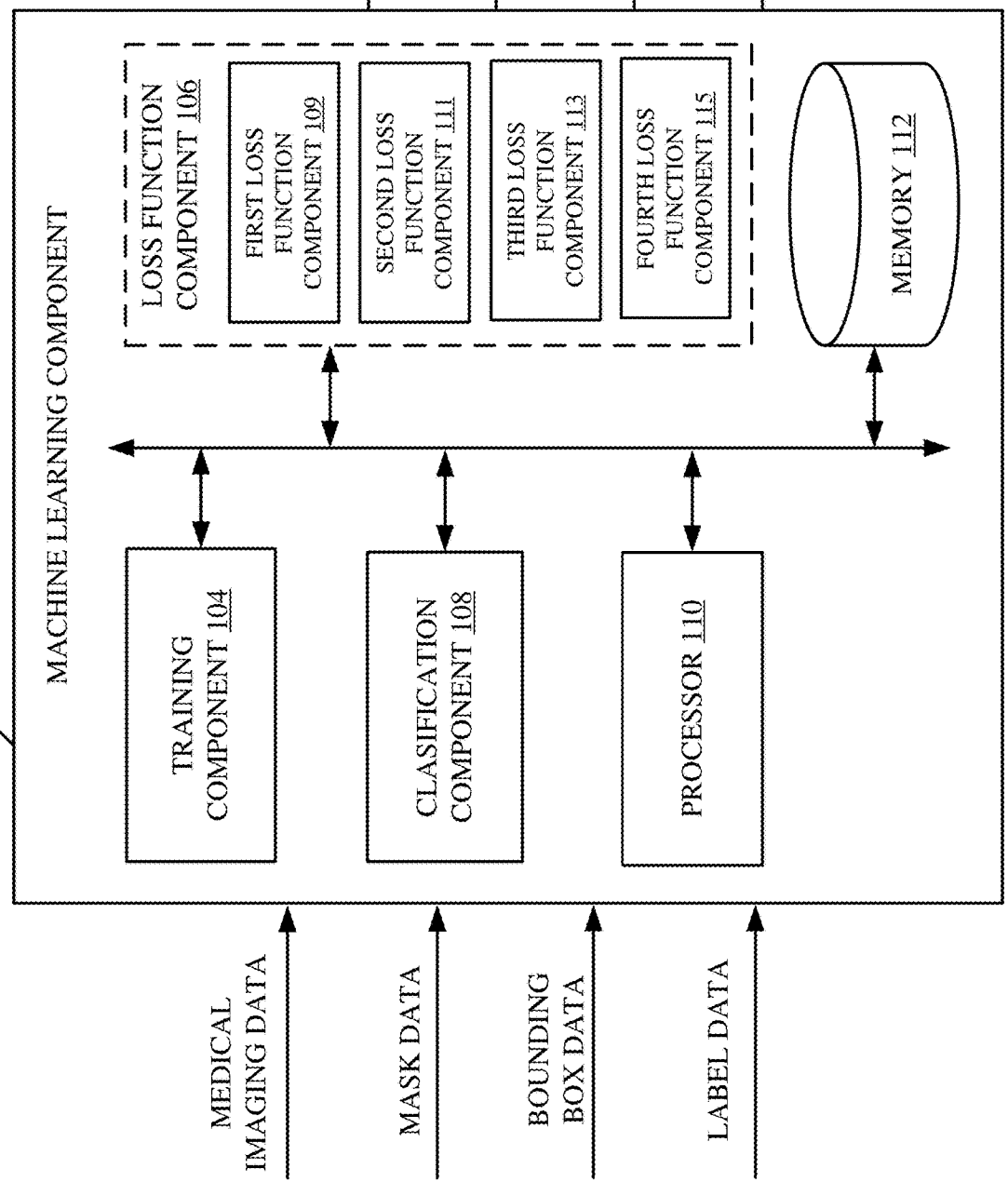
FIG. 1 illustrates a high-level block diagram of an example machine learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques that provide classification and/or localization based on annotation information are presented. For instance, a novel end-to-end deep learning framework is disclosed herein to, for example, automatically detect and/or localize a disease in medical images given mask annotations pertaining to regions of interest. The classification and localization network can be a fully convolutional neural network and can output the image-level label and localization map during inference. As such, classification and/or localization accuracy while using mask information can be improved, as compared to conventional classification using image-level labels only. In an embodiment, one or more image level labels, bounding boxes and/or masks pertaining to one or more regions of interest of an image can be employed, for example, to improve performance of a classifier. For instance, weighted losses from mask annotations, ground truth weak labels (e.g., image-level labels) and/or bounding boxes can be back propagated through the deep learning framework to, for example, back propagate classification loss and/or segmentation loss, and to also improve location results. Moreover, by employing the novel end-to-end deep learning framework as described herein, detection and/or localization of one or more features associated with image data (e.g., detection and/or localization of one or more conditions for a patient associated with medical imaging data) can be improved. Furthermore, accuracy and/or efficiency for classification and/or analysis of image data (e.g., medical imaging data) can be improved. Additionally, effectiveness of a machine learning model for classification and/or analysis of image data (e.g., medical imaging data) can be improved, performance of one or more processors that execute a machine learning model for classification and/or analysis of image data (e.g., medical imaging data) can be improved, and/or efficiency of one or more processors that execute a machine learning model for classification and/or analysis of image data (e.g., medical imaging data) can be improved.

Referring initially to FIG. 1, there is illustrated an example system 100 for classification and/or localization based on annotation information, according to an aspect of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a classification system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include a machine learning component 102 that can include a training component 104, a loss function component 106, and a classification component 108. In an embodiment, the loss function component 106 can include a first loss function component 109, a second loss function component 111, a third loss function component 113 and a fourth loss function component 115. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the machine learning component 102) can include memory 112 for storing computer executable components and instructions. The system 100 (e.g., the machine learning component 102) can further include a processor 110 to facilitate operation of the instructions (e.g., computer executable components and instructions) by the system 100 (e.g., the machine learning component 102).

The machine learning component 102 (e.g., the training component 104) can receive medical imaging data (e.g., MEDICAL IMAGING DATA shown in FIG. 1). The medical imaging data can be associated with the plurality of patients. Furthermore, the medical imaging data can be a set of images (e.g., a set of medical images). The medical imaging data can be two-dimensional medical imaging data and/or three-dimensional medical imaging data generated by one or more medical imaging devices. For instance, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an x-ray device, a computed tomography (CT) device, another type of medical imaging device, etc. Additionally or alternatively, the machine learning component 102 (e.g., the training component 104) can receive label data (e.g., LABEL DATA shown in FIG. 1). For instance, the medical imaging data can be associated with label data that includes a plurality of image level labels for a plurality of images. The plurality of image level labels included in the label data can be, for example, a plurality of ground truth weak labels for a plurality of images. Additionally or alternatively, the machine learning component 102 (e.g., the training component 104) can receive bounding box data (e.g., BOUNDING BOX DATA shown in FIG. 1). For instance, the medical imaging data can be associated with bounding box data that includes one or more bounding boxes that links one or more regions of interest in an image to a class label. A bounding box included in the bounding box data can identify where an object is located in an image and/or can link a region of interest associated with the object to a class label. A bounding box included in the bounding box data can include, for example, a set of coordinates (e.g., an upper left corner coordinate, an upper right corner coordinate, a lower left corner coordinate, a lower right corner coordinate, etc.) that provide a location (e.g., an area) for a region of interest. Furthermore, a bounding box included in the bounding box data can additionally or alternatively include a height value and/or a width value for a location (e.g., an area) associated with a region of interest. Additionally or alternatively, the machine learning component 102 (e.g., the training component 104) can receive mask data (e.g., MASK DATA shown in FIG. 1). In an embodiment, the mask data can be a set of masks from a plurality of objects. For example, each medical image from the medical imaging data can be associated with one or more masks. For instance, a mask can include one or more weights for one or more regions of interest in an image (e.g., in the medical imaging data). In one example, a mask can include a set of pixels that define a location for region of interests using binary filtering. In an embodiment, the medical imaging data and/or the mask data can be employed as training data to, for example, train a convolutional neural network. In certain embodiments, the medical imaging data and/or the mask data can be stored in a database that receives and/or stores training data associated with the at least one imaging device. In certain embodiments, the medical imaging data can be associated with a set of weights from a pre-trained model.

In an embodiment, the training component 104 can train a convolutional neural network based on the medical imaging data (e.g., a plurality of images) and/or the mask data. For instance, the training component 104 can perform a training phase for a machine learning process to, for example, train a neural network model for the convolutional neural network. The convolutional neural network can include a decoder consisting of at least one up-sampling layer and/or at least one convolutional layer. Additionally, in certain embodiments, the convolutional neural network can include a pretrained classifier network that outputs convolutional feature maps. Additionally or alternatively, in certain embodiments, the convolutional neural network can include a classification/localization network that outputs corresponding localization maps. In certain embodiments, the convolutional neural network can be a spring network of convolutional layers. For instance, the convolutional neural network can perform a plurality of sequential and/or parallel downsampling and upsampling of the medical imaging data associated with convolutional layers of the convolutional neural network. In an example, the convolutional neural network can perform a first convolutional layer process associated with sequential downsampling of the medical imaging data and a second convolutional layer process associated with sequential upsampling of the medical imaging data. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network can analyze the medical imaging data based on a first convolutional layer filter that comprises a first size, a second convolutional layer filter that comprises a second size that is different than the first size, and a third convolutional layer filter that comprises the first size associated with the first convolutional layer filter. In certain embodiments, the training component 104 can train the convolutional neural network based on the medical imaging data and/or the mask data (e.g., the training data) to determine whether a first class exists in the medical imaging data. Additionally or alternatively, the training component 104 can train the convolutional neural network based on the medical imaging data and/or the mask data (e.g., the training data) to form at least a portion of the convolutional neural network associated with a neural network architecture. The neural network architecture can be, for example, a binary neural network architecture that performs machine learning associated with one or more binary classifications for the medical imaging data.

The loss function component 106 can generate a loss function based on the plurality of masks associated with the medical imaging data, the plurality of image level labels, and/or the one or more bounding boxes. The loss function can be, for example, a loss function for the convolutional neural network. In certain embodiments, the loss function component 106 can employ the decoder to generate a localization map. For instance, the loss function component 106 can perform a decoding process associated with upsampling and/or one or more convolutional neural network layers to generate a localization map. The localization map can include, for example, information representing a probability score for one or more regions of the medical imaging data. In an embodiment, the localization map can include a visualization representing a probability score for one or more regions of the medical imaging data. In certain embodiments, the decoder can be a set of decoders. In an aspect, the decoder can be a set of decoders that perform distinct decoding processes associated with upsampling and/or or one or more convolutional neural network layers. For instance, the decoder can include a first decoder that performs a first decoding process associated with upsampling and/or or one or more convolutional neural network layers, a second decoder that performs a second decoding process associated with upsampling and/or or one or more convolutional neural network layers, a third decoder that performs a third decoding process associated with upsampling and/or or one or more convolutional neural network layers, etc. In another aspect, a number of decoders included in the set of decoders can be determined during training of the convolutional neural network.

The first loss function component 109 can generate a first loss function based on the plurality of masks associated with the medical imaging data. For instance, the first loss function component 109 can generate the first loss function based on a probability for a class associated with the plurality of masks. In one example, the first loss function component 109 can generate the first loss function based on a probability associated with classification output from the convolutional neural network and the plurality of masks. The second loss function component 111 can generate a second loss function based on the plurality of image level labels associated with the medical imaging data (e.g., a plurality of images). For instance, the second loss function component 111 can generate the second loss function based on a probability for a class associated with the plurality of image level labels. In one example, the second loss function component 111 can generate the second loss function based on a probability associated with classification output from the convolutional neural network and the plurality of image level labels. The third loss function component 113 can generate a third loss function based on the one or more bounding boxes. The one or more bounding boxes can link one or more regions of interest to one or more class labels. In one example, the third loss function component 113 can generate the third loss function based on a bounding box that links a region of interest in an image to a class label. The fourth loss function component 115 can generate a fourth loss function based on the first loss function, the second loss function and/or the third loss function. For instance, the fourth loss function component 115 can apply a first weight to the first loss function, can apply a second weight to the second loss function, and/or can apply a third weight to the third loss function. Additionally, the fourth loss function component 115 can combine the first loss function, the second loss function, and/or the third loss function (e.g., the fourth loss function component 115 can add the first loss function, the second loss function, and/or the third loss function together). In one example, the second weight can be different than the first weight and/or the third weight. In another example, the second weight can correspond to the first weight and/or the third weight. In an aspect, the fourth loss function can be iteratively back propagated to tune one or more parameters of the convolutional neural network. For example, the convolutional neural network can be modified based on the fourth loss function to improve the classification output from the convolutional neural network. In certain embodiments, the machine learning component 102 (e.g., the loss function component 106) can generate loss function data that includes the first loss function, the second loss function, the third loss function and/or the fourth loss function generated by the loss function component 106. For example, the loss function data can include the first loss function associated with the plurality of masks, the second loss function associated with the plurality of image level labels, the third loss function associated with the bounding box, and/or the fourth loss function that can be employed to tune one or more parameters of the convolutional neural network.

The classification component 108 can predict a classification label for an input image based on the convolutional neural network. In an embodiment, the classification component 108 can generate classification data (e.g., CLASSIFICATION DATA shown in FIG. 1) that can include the classification label for the input image. Additionally or alternatively, the classification component 108 can generate localization data (e.g., LOCALIZATION DATA shown in FIG. 1) that can include a localization map for the input image. The localization map for the input image can include, for example, information representing a probability score for one or more regions of the input image. In an embodiment, the localization map for the input image can include a visualization representing a probability score for one or more regions of the input image. Additionally or alternatively, the classification component 108 can generate predicted bounding box data (e.g., PREDICTED BOUNDING BOX DATA shown in FIG. 1). The predicted bounding box data can be a bounding box for the input image that links one or more regions of interest in the input image to one or more class labels associated with the input image. In an aspect, the predicted bounding box for the input image can provide a location for a region of interest in the input image. Additionally or alternatively, the classification component 108 can generate predicted mask data (e.g., PREDICTED MASK DATA shown in FIG. 1). The predicted mask data can include a set of masks for the input image. For instance, the predicted mask data can include one or more weights for one or more regions of interest in the input image. In one example, predicted mask data can include a set of pixels that define a location for one or more region of interests in the input image using, for example, binary filtering. The convolutional neural network employed by the classification component 108 can be a version of the convolutional neural that is tuned based on the fourth loss function. The input image can be, for example, a medical image. The input image can be a two-dimensional image (e.g., a two-dimensional medical image) and/or three-dimensional image (e.g., a three-dimensional medical image) generated by one or more medical imaging devices. For instance, the input image can be a two-dimensional image (e.g., a two-dimensional medical image) and/or three-dimensional image (e.g., a three-dimensional medical image) generated by an x-ray device, a CT device, another type of medical imaging device, etc. In one example, the input image can be an electromagnetic radiation image captured via a set of sensors (e.g., a set of sensors associated with a medical imaging device). In certain embodiments, the input image can be a series of electromagnetic radiation images captured via a set of sensors (e.g., a set of sensors associated with a medical imaging device) during an interval of time. The input image can be received directly from one or more medical imaging devices. Alternatively, the input image can be stored in one or more databases that receives and/or stores the input image associated with the one or more medical imaging devices. In an aspect, the convolutional neural network can include a classification/localization network that outputs corresponding localization maps based on the convolutional feature maps. In another aspect, a size of a bounding box from the one or more bounding boxes can be matched with a size of a convolutional feature map from the convolutional feature maps. In yet another aspect, a size of a mask from the plurality of masks can be matched with a size of a convolutional feature map from the convolutional feature maps. Additionally or alternatively, a size of a mask from the plurality of masks can be matched with a size of a convolutional feature map from the convolutional feature maps based on a mask pooling process.

In certain embodiments, the classification component 108 can extract information that is indicative of correlations, inferences and/or expressions from the input image based on the convolutional neural network (e.g., a version of the convolutional neural that is tuned based on the fourth loss function). The classification component 108 can generate the learned imaging output based on the execution of at least one machine learning model associated with the convolutional neural network (e.g., a version of the convolutional neural that is tuned based on the fourth loss function). In an aspect, the classification component 108 can generate learned imaging output. The learned imaging output generated by the classification component 108 can include, for example, learning, correlations, inferences and/or expressions associated with the input image. In an aspect, the classification component 108 can perform learning with respect to the input image explicitly or implicitly using the convolutional neural network (e.g., a version of the convolutional neural that is tuned based on the fourth loss function). The classification component 108 can also employ an automatic classification system and/or an automatic classification process to facilitate analysis of the input image. For example, the classification component 108 can employ a probabilistic and/or statistical-based analysis (e.g., factoring into the analysis utilities and costs) to learn and/or generate inferences with respect to the input image. The classification component 108 can employ, for example, a support vector machine (SVM) classifier to learn and/or generate inferences for imaging data. Additionally or alternatively, the classification component 108 can employ other classification techniques associated with Bayesian networks, decision trees and/or probabilistic classification models. Classifiers employed by the classification component 108 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, x=(x1, x2, x3, x4, xn), to a confidence that the input belongs to a class—that is, f(x)=confidence(class).

It is to be appreciated that technical features of the machine learning component 102 are highly technical in nature and not abstract ideas. Processing threads of the machine learning component 102 that process and/or analyze the medical imaging data, determine outlier medical imaging data, etc. cannot be performed by a human (e.g., are greater than the capability of a single human mind). For example, the amount of the medical imaging data processed, the speed of processing of the medical imaging data and/or the data types of the medical imaging data processed by the machine learning component 102 over a certain period of time can be respectively greater, faster and different than the amount, speed and data type that can be processed by a single human mind over the same period of time. Furthermore, the medical imaging data processed by the machine learning component 102 can be one or more medical images generated by sensors of a medical imaging device. Moreover, the machine learning component 102 can be fully operational towards performing one or more other functions (e.g., fully powered on, fully executed, etc.) while also processing the medical imaging data.

Figure 2:
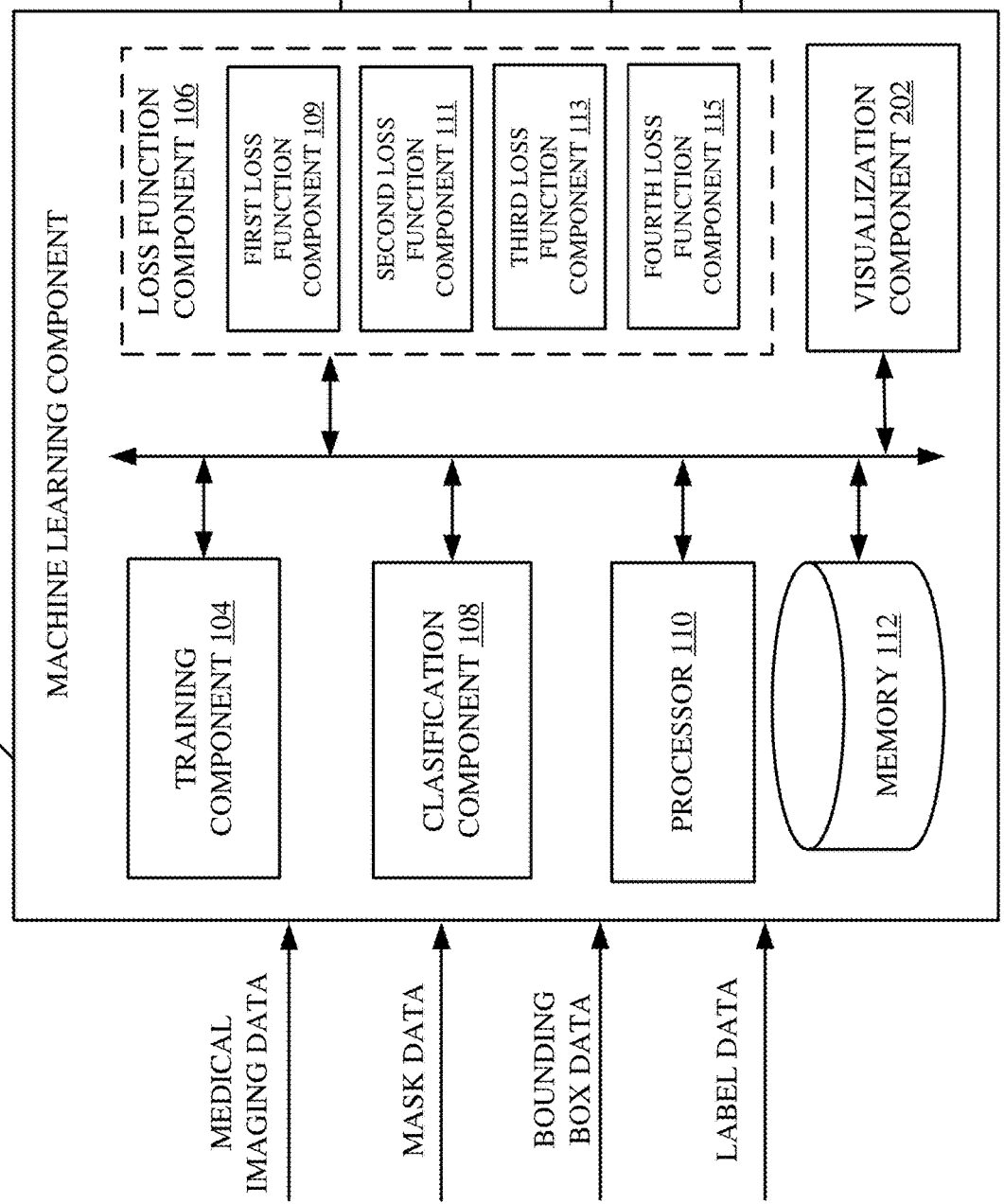
FIG. 2 illustrates a high-level block diagram of another example machine learning component, in accordance with various aspects and implementations described herein.

Referring now to FIG. 2, there is illustrated a non-limiting implementation of a system 200 in accordance with various aspects and implementations of this disclosure. Repetitive description of like elements employed in other embodiments described herein is omitted for sake of brevity.

The system 200 includes the machine learning component 102. The machine learning component 102 can include the training component 104, the loss function component 106, the classification component 108, a visualization component 202, the processor 110 and/or the memory 112. In an embodiment, the loss function component 106 can include the first loss function component 109, the second loss function component 111, the third loss function component 113 and/or the fourth loss function component 115. The visualization component 202 can generate a multi-dimensional visualization associated with the classification label for the input image classified by the classification component 108. Additionally or alternatively, the visualization component 202 can generate a multi-dimensional visualization associated with localization information for the input image classified by the classification component 108. For instance, the visualization component 202 can generate a human-interpretable visualization of the classification label for the input image and/or the localization information for the input image. Additionally or alternatively, the visualization component 202 can generate a human-interpretable visualization of the input image and/or the medical imaging data. In an embodiment, the visualization component 202 can generate deep learning data based on a classification and/or a localization for a portion of an anatomical region associated with the input image. The deep learning data can include, for example, a classification and/or a location for one or more diseases located in the input image. In certain embodiments, the deep learning data can include probability data indicative of a probability for one or more diseases being located in the input image. The probability data can be, for example, a probability array of data values for one or more diseases being located in the input image. Additionally or alternatively, the visualization component 202 can generate a multi-dimensional visualization associated with classification and/or localization for a portion of an anatomical region associated with the input image.

The multi-dimensional visualization can be a graphical representation of the input image that shows a classification and/or a location of one or more diseases with respect to a patient body. The visualization component 202 can also generate a display of the multi-dimensional visualization of the diagnosis provided by a medical imaging diagnosis process. For example, the visualization component 202 can render a 2D visualization of a portion of an anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In an aspect, the multi-dimensional visualization can include deep learning data. In another aspect, the deep learning data can also be rendered on the 3D model as one or more dynamic visual elements. The visualization component 202 can, in an embodiment, alter visual characteristics (e.g., color, size, hues, shading, etc.) of at least a portion of the deep learning data associated with the multi-dimensional visualization based on the classification and/or the localization for the portion of the anatomical region. For example, the classification and/or the localization for the portion of the anatomical region can be presented as different visual characteristics (e.g., colors, sizes, hues or shades, etc.), based on a result of deep learning and/or medical imaging diagnosis. In another aspect, the visualization component 202 can allow a user to zoom into or out with respect to the deep learning data associated with the multi-dimensional visualization. For example, the visualization component 202 can allow a user to zoom into or out with respect to a classification and/or a location of one or more diseases identified in the anatomical region of the patient body. As such, a user can view, analyze and/or interact with the deep learning data associated with the multi-dimensional visualization for the input image.

Figure 3:
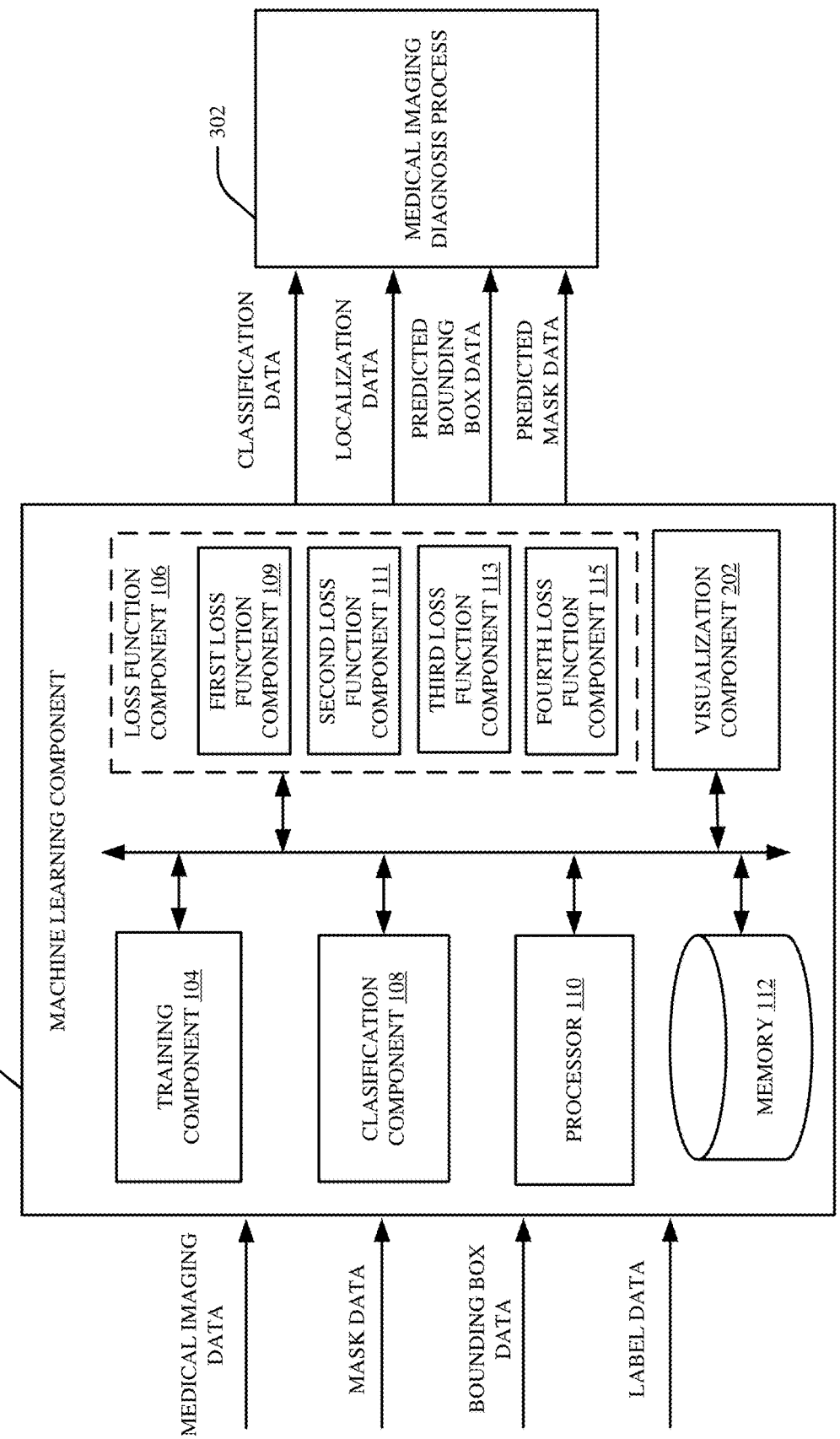
FIG. 3 illustrates a system that includes an example machine learning component and an example medical imaging diagnosis process, in accordance with various aspects and implementations described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity.

The system 300 includes the machine learning component 102 and medical imaging diagnosis process 302. The machine learning component 102 can provide the classification data and/or the localization data to the medical imaging diagnosis process 302. The classification data and/or the localization data can include one or more classifications and/or localization information associated with the input image. In an aspect, the classification data and/or the localization data can be generated by the classification component 108. Additionally or alternatively, in certain embodiments, the machine learning component 102 can provide the predicted bounding box data and/or the predicted mask data to the medical imaging diagnosis process 302. In an embodiment, the medical imaging diagnosis process 302 can perform deep learning to facilitate classification and/or localization of one or more diseases associated with the input image and/or the medical imaging data. In another aspect, the medical imaging diagnosis process 302 can perform deep learning based on a convolutional neural network that receives the input image and/or the medical imaging data. A disease classified and/or localized by the medical imaging diagnosis process 302 can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an aspect, the medical imaging diagnosis process 302 can determine a prediction for a disease associated with the input image and/or the medical imaging data. For example, the medical imaging diagnosis process 302 can determine a probability score for a disease associated with the input image and/or the medical imaging data (e.g., a first percentage value representing likelihood of a negative prognosis for the disease and a second value representing a likelihood of a positive prognosis for the disease).

Figure 4:
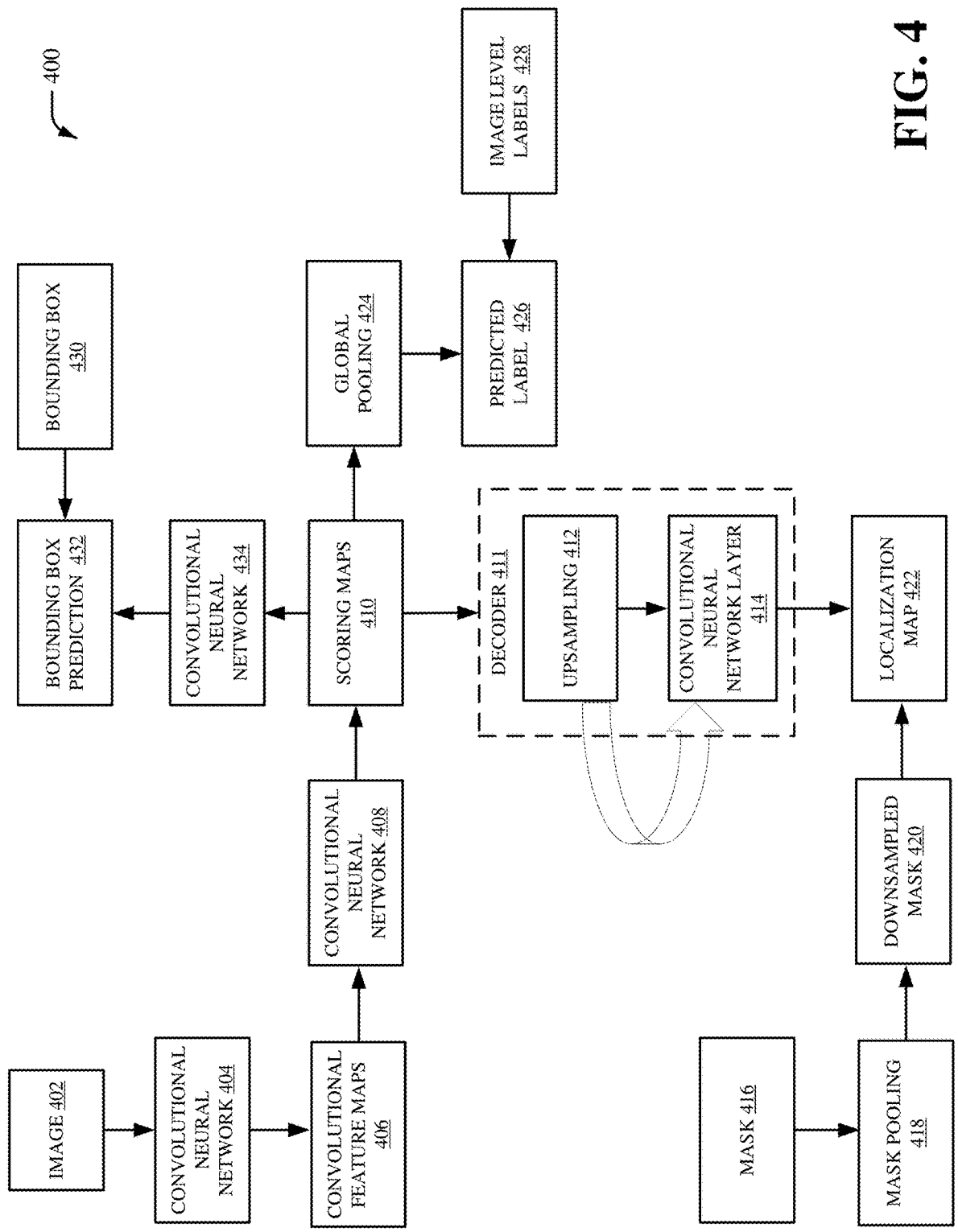
FIG. 4 illustrates another example system associated with a segmentation-classification network, in accordance with various aspects and implementations described herein.

Referring now to FIG. 4, there is illustrated a non-limiting implementation of a system 400 in accordance with various aspects and implementations of this disclosure. Repetitive description of like elements employed in other embodiments described herein is omitted for sake of brevity.

The system 400 can be a classification-localization network. In an embodiment, the system 400 can represent a machine learning process and/or another process performed by the machine learning component 102 (e.g., the training component 104, the loss function component 106, the classification component 108, and/or the visualization component 202). An image 402 (e.g., an input image) can be processed by a convolutional neural network 404. The image 402 can be, for example, a medical image. For instance, the image 402 can be a two-dimensional image (e.g., a two-dimensional medical image) and/or three-dimensional image (e.g., a three-dimensional medical image) generated by one or more medical imaging devices. In one example, the image 402 can be a two-dimensional image (e.g., a two-dimensional medical image) and/or three-dimensional image (e.g., a three-dimensional medical image) generated by an x-ray device, a CT device, another type of medical imaging device, etc. In another example, the image 402 can be an electromagnetic radiation image captured via a set of sensors (e.g., a set of sensors associated with a medical imaging device). In certain embodiments, the image 402 can be a series of electromagnetic radiation images captured via a set of sensors (e.g., a set of sensors associated with a medical imaging device) during an interval of time. The image 402 can be received directly from one or more medical imaging devices. Alternatively, the image 402 can be stored in one or more databases that receives and/or stores the image 402 associated with the one or more medical imaging devices. In an embodiment, the image 402 can be an input image analyzed by the machine learning component 102 (e.g., an input image classified by the classification component 108).

The convolutional neural network 404 can output convolutional feature maps 406, which can be employed by a convolutional neural network 408 (e.g., a classification and localization network) that creates scoring maps 410. In an aspect, the convolutional neural network 404 can encode the image 402 into the convolutional feature maps 406. In an embodiment, the convolutional neural network 404 can be a spring network of convolutional layers. For instance, the convolutional neural network can perform a plurality of sequential and/or parallel downsampling and upsampling of the image 402 associated with convolutional layers of the convolutional neural network 404 to generate the convolutional feature maps 406. In an example, the convolutional neural network 404 can perform a first convolutional layer process associated with sequential downsampling of the image 402 and a second convolutional layer process associated with sequential upsampling of the image 402 to generate the convolutional feature maps 406. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network 404 can analyze the image 402 based on a first convolutional layer filter that comprises a first size, a second convolutional layer filter that comprises a second size that is different than the first size, and a third convolutional layer filter that comprises the first size associated with the first convolutional layer filter to generate the convolutional feature maps 406. The convolutional feature maps 406 can be, for example, data that represent output of convolutional layer filters applied to a previous convolutional layer. For example, a first convolutional feature map from the convolutional feature maps 406 can include first data that represents output of a first convolutional layer filter applied to a previous convolutional layer, a second convolutional feature map from the convolutional feature maps 406 can include second data that represents output of a second convolutional layer filter applied to a previous convolutional layer, a third convolutional feature map from the convolutional feature maps 406 can include third data that represents output of a third convolutional layer filter applied to a previous convolutional layer, etc. In another embodiment, the convolutional neural network 408 can be a 1×1 convolutional layer that generates the scoring maps 410 based on the convolutional feature maps 406. The scoring maps 410 can include prediction scores for a class associated with regions of interest for the image 402.

In an aspect, during training of the convolutional neural network 404, a mask 416 of the image 402 can be matched with a size of the convolutional feature maps 406 via mask pooling 418. For instance, the mask pooling 418 can compare the mask 516 with the downsampled mask 420 (e.g., the predicted mask). A size of the downsampled mask 420 can, for example correspond to a size of the mask 416. In one example, during training of the convolutional neural network 404, the mask 416 can be a mask of a region of interest for the image 402 that is matched with a size of at least one convolutional feature map from the convolutional feature maps 406. Furthermore, the mask pooling 418 can perform rational mask pooling to compare the mask 416 (e.g., the predicted mask) with the downsampled mask 420 (e.g., the downsampled ground truth mask) of the same size. In an embodiment, a class label for the image 402 can be implicit and can be determined based on the mask 416. For example, a mask element associated with the mask 416 that is above a defined threshold can signal presence of a class. For testing, the scoring maps 410 can provide a predicted classification label with a localization map 422. The localization map 422 can include, for example, information representing a probability score for one or more regions of the image 402. In certain embodiments, the localization map 422 can include a visualization representing a probability score for one or more regions of the image 402.

The system 400 can also include a decoder 411. The decoder 411 can include upsampling 412 and/or a convolutional neural network layer 414. In an aspect, the decoder 411 can be implemented as a repeatable segmentation network where the upsampling 412 and the convolutional neural network layer 414 can be repeated blocks a certain number of times. In another aspect, the decoder 411 can generate the localization map 422. For instance, the decoder 411 can perform a decoding process associated with the upsampling 412 and/or the convolutional neural network layer 414 to generate the localization map 422. The decoder 411 can provide improved localization results associated with the image 402. In an embodiment, a number of decoder blocks associated with the decoder 411 can be treated as a hyperparameter during training of the convolutional neural network 404. In another embodiment, the upsampling 412 can perform bilinear interpolation to upsample the scoring maps 412 to a certain size. In yet another embodiment, the convolutional neural network layer 414 can be configured as a recognition network that includes a set of filters, a batch normalization process and/or a set of rectified linear units to generate a set of predictions for the localization map 422. The decoder 411 can also provide smoother and more accurate heat maps in a final classification and/or localization result for the image 402. In another aspect, the system 400 can provide improved the performance of a classifier based on the mask 416 pertaining to regions of interest and/or image level labels for the image 402.

The system 400 can also include global pooling 424, predicted label 426 and/or image level labels 428 to facilitate improved classification accuracy when given weak and richer annotation information. The global pooling 424 can perform a global pooling process (e.g., a global average pooling process) associated with the scoring maps 410. For instance, the global pooling 424 can modify dimensionality (e.g., reduce dimensionality or increase dimensionality) of the scoring maps 410. The predicted label 426 can be generated based on the scoring maps 410 and the image level labels 428. For instance, the image level labels 428 and the global pooling 424 of the scoring maps 410 can be employed to generate the predicted label 426. The image level labels 428 can be a set of labels for a set of images where each image is annotated with a label. A label can be a description (e.g., a textual description of a disease, etc.) associated with an image. For example, an image associated with the image level labels 428 can be labeled with a particular disease included in the image. The predicted label 426 can include one or more predicted classes for the scoring maps 410. For example, the predicted label 426 can be a set of predicted class labels for the scoring maps 410. In an embodiment, the system 400 can also include a bounding box 430. The bounding box 430 can include one or more bounding boxes. For instance, the bounding box 430 can be one or more bounding boxes that can link one or more regions of interest to one or more class labels associated with the predicted label 426 and/or the image level labels 428. In one example, the bounding box 430 can link a region of interest in the image 402 to a class label associated with the predicted label 426 and/or the image level labels 428. In an aspect, a size of the bounding box 430 can be matched to a size of the convolutional feature maps 406. For instance, the bounding box 430 can provide a location for a region of interest in the image 402 and a size of the bounding box 430 can be matched with a size of at least one convolutional feature map from the convolutional feature maps 406. In an embodiment, the bounding box 430 can be employed to generate bounding box prediction 432. The bounding box prediction 432 can be, for example, a predicted bounding box. For example, the bounding box 430 can be a ground truth bounding box and the bounding box prediction 432 can be a predicted bounding box. In an aspect, the bounding box prediction 432 can provide a prediction for the bounding box 430 using, for example, an object detection technique. In certain embodiments, the bounding box prediction 432 can be generated based on a convolutional neural network 434. The convolutional neural network 434 can, for example, a 1×1 convolutional layer that facilitates object detection within the image 402.

Figure 5:
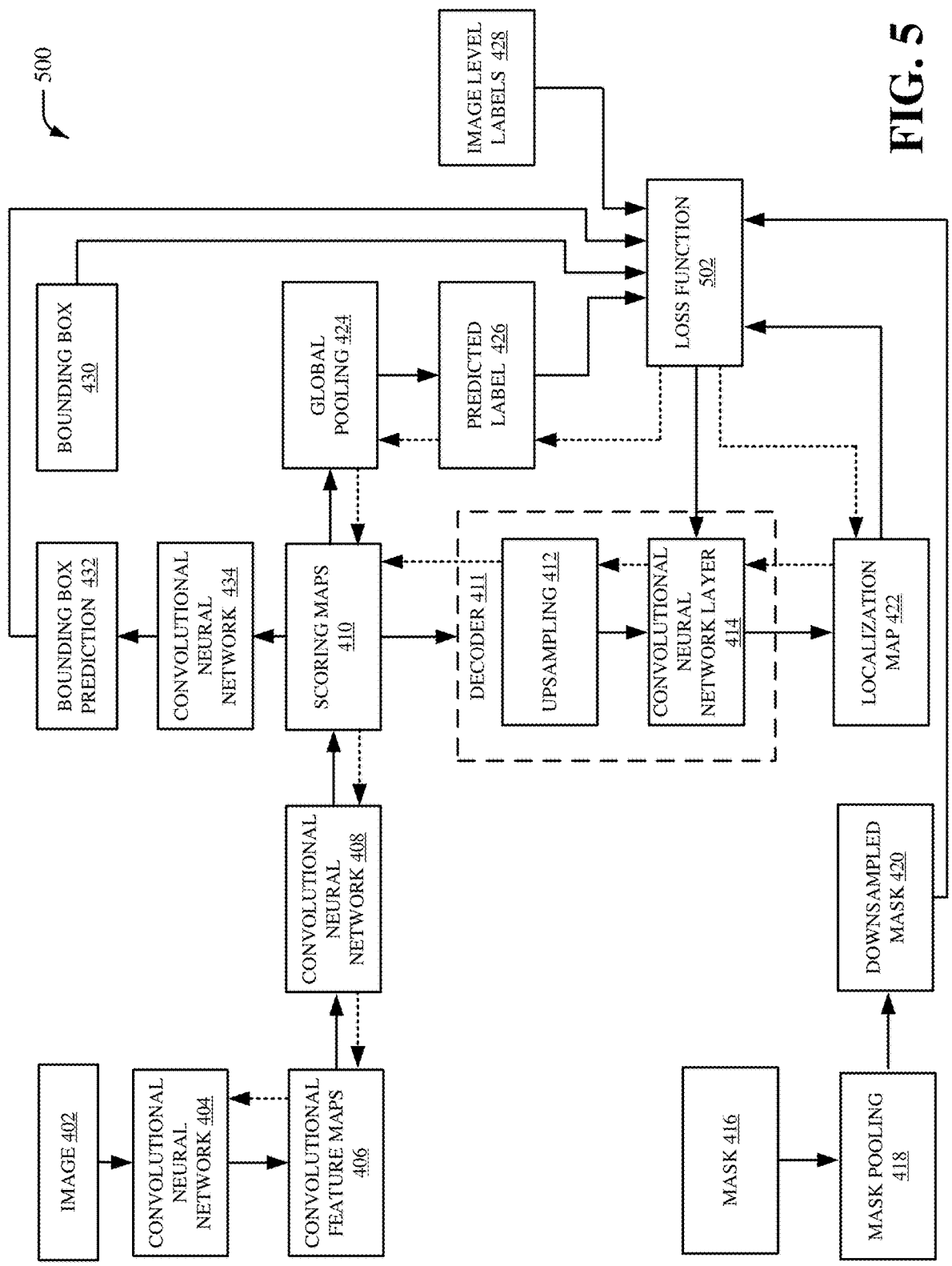
FIG. 5 illustrates another example system associated with a segmentation-classification network implementing a loss function, in accordance with various aspects and implementations described herein.

Referring now to FIG. 5, there is illustrated a non-limiting implementation of a system 500 in accordance with various aspects and implementations of this disclosure. Repetitive description of like elements employed in other embodiments described herein is omitted for sake of brevity.

The system 500 can be a classification-localization network that includes a loss function 502. In an embodiment, the system 500 can represent a machine learning process and/or another process performed by the machine learning component 102 (e.g., the training component 104, the loss function component 106, the first loss function component 109, the second loss function component 111, the third loss function component 113, the fourth loss function component 115, the classification component 108, and/or the visualization component 202). The system 500 can include the image 402, the convolutional neural network 404, the convolutional feature maps 406, the convolutional neural network 408, the scoring maps 410, and the decoder 411 that includes the upsampling 412 and the convolutional neural network layer 414. The system 500 can also include the mask 416, the mask pooling 418, the downsampled mask 420, the localization map 422, the global pooling 424, the predicted label 426, the image level labels 428, the bounding box 430, the bounding box prediction 432, the convolutional neural network 434, and the loss function 502. The loss function 502 can be a loss function that is created based on the downsampled mask 420 (e.g., a downsampled ground truth mask) and the mask 416 (e.g., a predicted mask) during training of the convolutional neural network 404. Additionally or alternatively, the loss function 502 can be created based on the predicted label 426 and/or the image level labels 428. Additionally or alternatively, the loss function 502 can be created based on the bounding box 430 and/or the bounding box prediction 432. In an embodiment, the loss function 502 can correspond to the fourth loss function generated by the fourth loss function component 115. The loss function 502 can, for example, be represented by the following equation:

$$\text{Loss} = \lambda_{mask}\eta \text{Loss}_{mask} + \lambda_{bbx}(1-\eta)\gamma \text{Loss}_{bbx} + \lambda_{label}(1-\eta)(1-\gamma)\text{Loss}_{label}$$

where $\text{Loss}_{mask}$ can correspond to the first loss function associated with the plurality of masks, $\text{Loss}_{label}$ can correspond to the second loss function associated with the plurality of image level labels, and $\text{Loss}_{bbx}$ can correspond to the third loss function associated with the one or more bounding boxes. Furthermore, $\lambda_{mask}$ can be a first weight for the first loss function $\text{Loss}_{mask}$, $\lambda_{label}$ can be a second weight for the second loss function $\text{Loss}_{label}$, and $\lambda_{bbx}$ can be a third weight for the third loss function $\text{Loss}_{bbx}$. In addition, $\eta$ can be a variable that indicates whether a mask exists and $\gamma$ can be a variable that indicates whether a bounding box exists. For example, the variable $\eta$ can have a value equal to 0 or 1 depending on whether a mask exists, and the variable $\gamma$ can have a value equal to 0 or 1 depending on whether a bounding box exists. In an embodiment, the first loss function $\text{Loss}_{mask}$ can be equal to:

$$-\Sigma_i \log(p(y_k|x_i, \text{mask}_i^k))$$

where $p(y_k|x_i, \text{mask}_i^k)$ is a probability of an image i being positive for class k with respect to a total area in image i and/or a region covered by a mask. Additionally, the second loss function $\text{Loss}_{label}$ can be equal to:

$$-\Sigma_i \log(p(y_k|x_i, \text{labels}_i^k))$$

where $p(y_k|x_i, \text{labels}_i^k)$ is a probability of an image i being positive for class k with respect to a total area in image i and/or a region covered by an image-level label. Additionally, the third loss function $\text{Loss}_{bbx}$ can be equal to:

$$-\Sigma_i \log(p(y_k|x_i, \text{bbx}_i^k))$$

where $p(y_k|x_i, \text{bbx}_i^k)$ is a probability of an image i being positive for class k with respect to a total area in image i and/or a region of interest covered by a bounding box. $\text{Loss}_{mask}$ can correspond to the first loss function generated by the first loss function component 109, $\text{Loss}_{labels}$ can correspond to the second loss function generated by the second loss function component 111, $\text{Loss}_{bbx}$ can correspond to the third loss function generated by the third loss function component 113, and Loss can correspond to the fourth loss function generated by the fourth loss function component 115. In an embodiment, Loss (e.g., the fourth loss function) can be equal to $w_1 * \text{Loss}_{labels} + w_2 * \text{Loss}_{mask} + w_3 * \text{Loss}_{bbx}$, where $w_1$ is a first weight, $w_2$ is a second weight and $w_3$ is a third weight. Furthermore, $y_k$ can be a kth output from the convolutional neural network 404 that denotes whether the image i is positive for class k, where $x_i$ is an ith image. In an embodiment, the loss function 502 can be generated based on the downsampled mask 420, the localization map 422, the predicted label 426 and/or the image level labels 428. For instance, the loss function 502 can be generated based on a first probability for a class associated with the downsampled mask 420, the localization map 422. Additionally or alternatively, the loss function 502 can be generated based on a second probability for a class associated with the predicted label 426, the image level labels 428 and/or the localization map 422. Additionally or alternatively, the loss function 502 can be generated based on a third probability class for a class associated with the bounding box 430 and/or the bounding box prediction 432. Furthermore, the loss function 502 can be provided to the convolutional neural network layer 414. Additionally, the loss function 502 can be back propagated from the convolutional neural network layer 414 to the convolutional neural network 404. For instance, the loss function 502 can be back propagated through the system 500 starting from the convolutional neural network layer 414 and ending at the convolutional neural network 404. In an embodiment, the loss function 502 can be back propagated through the localization map 422, the convolutional neural network layer 414, the upsampling 412, the scoring maps 410, the convolutional neural network 408, the convolutional feature maps 406 and/or the convolutional neural network 404. Additionally or alternatively, the loss function 502 can be back propagated through the predicted label 426, the global pooling 424, the scoring maps 410, the convolutional neural network 408, the convolutional feature maps 406 and/or the convolutional neural network 404. As such, weighted losses associated with the image level labels 428 and/or the downsampled mask 420 can back propagate classification loss and/or segmentation loss associated with the convolutional neural network 404. In an aspect, the loss function 502 can tune one or more parameters of the convolutional neural network 404. For example, the convolutional neural network 404 can be modified based on the loss function 502 to improve classification and/or localization results associated with the localization map 422.

Figure 6:
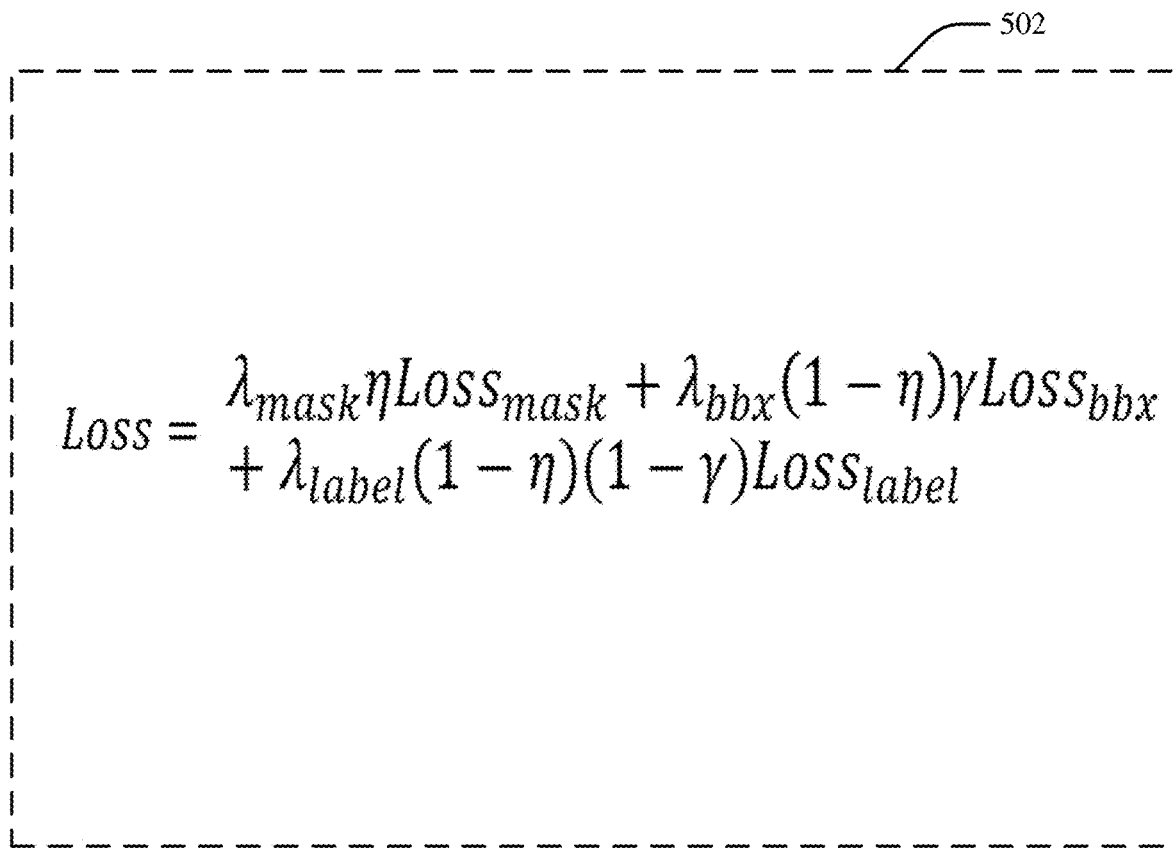
FIG. 6 illustrates an example loss function, in accordance with various aspects and implementations described herein.

Referring now to FIG. 6, there is illustrated a non-limiting example of the loss function 502 in accordance with various aspects and implementations of this disclosure. Repetitive description of like elements employed in other embodiments described herein is omitted for sake of brevity.

As discussed above, the loss function 502 can be represented by the following equation:

$$\text{Loss} = \lambda_{mask}\eta\text{Loss}_{mask} + \lambda_{bbx}(1-\eta)\gamma\text{Loss}_{bbx} + \lambda_{label}(1-\eta)(1-\gamma)\text{Loss}_{label}$$

For instance, the loss function 502 can be generated based on a first probability for a class associated with the downsampled mask 420 and/or the localization map 422. Additionally or alternatively, the loss function 502 can be generated based on a second probability for a class associated with the predicted label 426, the image level labels 428 and/or the localization map 422. Additionally or alternatively, the loss function 502 can be generated based on a third probability for a class associated with the bounding box 430 and/or the bounding box prediction 432. By employing the loss function 502 and/or annotation information (e.g. the mask 416 and/or the downsampled mask 420), classification accuracy can be improved. The system 400 and/or the system 500 can also output improved localization maps (e.g., more accurate localization maps). For example, the loss function 502 and/or annotation information (e.g. the mask 416 and/or the downsampled mask 420) can be employed to provide improved localization information associated with the localization map 422.

In a non-limiting embodiment that employs the system 400 and/or the system 500, experiments on a dataset can consist of a medical condition and non-medical condition X-ray images that are extracted from a database. A medical condition can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, pneumothorax, or another type of medical condition associated with an anatomical region of a patient body. The medical condition masks can be annotated, for example, by radiologists. A total of 1806 images can be split to 1444 images for training (e.g., 80% of the images), 180 images for validation (e.g., 10% of the images) and 182 images for testing (10% of the images), as shown below in Table I. Experimental results are shown below in Table II. Testing accuracy of the system 400 and/or the system 500 is 0.923 and AUC is 0.979 with dice coefficient 0.5, which outperforms a conventional classification network trained only with image-level labels.

TABLE I

Description of medical condition dataset

| Dataset | Training (80%) | Validation (10%) | Testing (10%) |
| --- | --- | --- | --- |
| Medical Condition | 722 | 90 | 91 |
| Non-Medical Condition | 722 | 90 | 91 |
| Total | 1444 | 180 | 182 |

According, as seen from experimental results in Table II, by providing richer annotation information (e.g. masks), classification accuracy can be improved and a convolutional neural network can also output improved localization maps (e.g., more accurate localization maps). This can be achieved by the same underlying prediction model for both tasks. The system 400 and/or the system 500 can also be flexible and can be generalized to other applications due to a selectable convolutional neural network framework associated with the system 400 and/or the system 500, a repeatable segmentation network associated with the system 400 and/or the system 500, and a tunable mask size associated with the system 400 and/or the system 500. As such, the system 400 and/or the system 500 can jointly model classification and/or localization. Furthermore, the system 400 and/or the system 500 can apply the classification and/or the localization to disease detection (e.g., medical condition detection, etc.) in medical imaging data (e.g., X-ray images) and/or other digital images.

Figure 7:
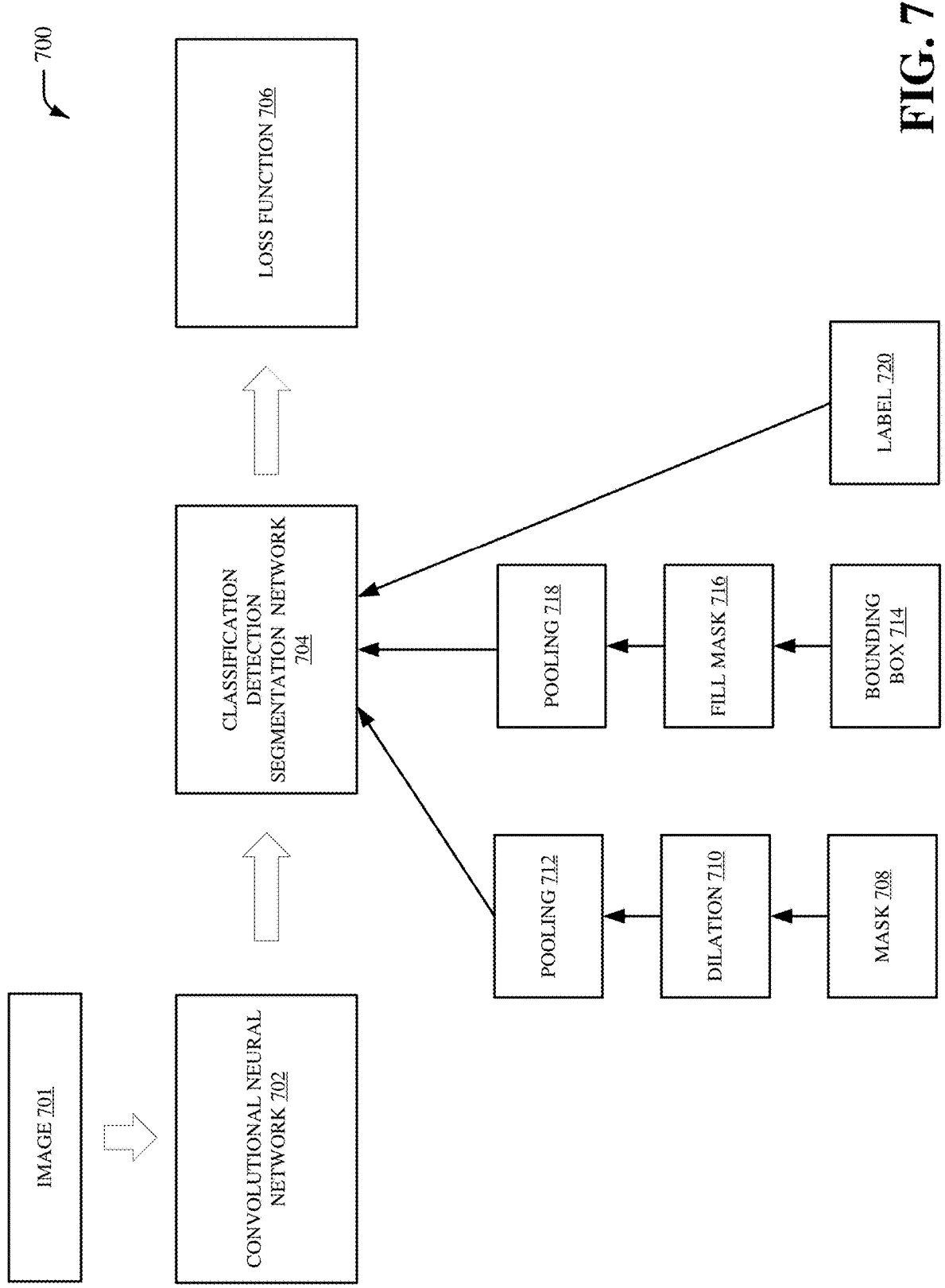
FIG. 7 illustrates an example system that employs a mask, a bounding box and/or a label to generate a loss function, in accordance with various aspects and implementations described herein.

Referring now to FIG. 7, there is illustrated a non-limiting implementation of a system 700 in accordance with various aspects and implementations of this disclosure. Repetitive description of like elements employed in other embodiments described herein is omitted for sake of brevity.

The system 700 includes a convolutional neural network 702, a classification detection segmentation network 704 and a loss function 706. The convolutional neural network 702 can be a deep artificial neural network associated with machine learning. In an embodiment, the convolutional neural network 702 can encode an image 701 into a set of convolutional feature maps. The image 701 can be, for example, an input image for the convolutional neural network 702. In an embodiment, the image 701 can be a medical image. For instance, the image 701 can be a two-dimensional image (e.g., a two-dimensional medical image) and/or three-dimensional image (e.g., a three-dimensional medical image) generated by one or more medical imaging devices. In one example, the image 701 can be a two-dimensional image (e.g., a two-dimensional medical image) and/or three-dimensional image (e.g., a three-dimensional medical image) generated by an x-ray device, a CT device, another type of medical imaging device, etc. In another example, the image 701 can be an electromagnetic radiation image captured via a set of sensors (e.g., a set of sensors associated with a medical imaging device). In certain embodiments, the image 701 can be a series of electromagnetic radiation images captured via a set of sensors (e.g., a set of sensors associated with a medical imaging device) during an interval of time. The image 701 can be received directly from one or more medical imaging devices. Alternatively, the image 701 can be stored in one or more databases that receives and/or stores the image 701 associ-

TABLE II

| | Experimental Results | | | | | | | | |
| --- | --- | --- | --- | --- | --- | --- | --- | --- | --- |
| Model | val Accuracy | val Precision | val Recall | val AUC | val Dice | test Accuracy | test Precision | test Recall | test AUC |
| Conventional Classification Network | 0.894 | 0.899 | 0.889 | 0.941 | | 0.896 | 0.875 | 0.923 | 0.945 |
| System 400 and/or System 500 | 0.95 | 0.966 | 0.933 | 0.98 | 0.518 | 0.923 | 0.953 | 0.89 | 0.979 | ated with the one or more medical imaging devices. In an embodiment, the image 701 can correspond to the image 402 and/or the medical imaging data received by the machine learning component 102.

In certain embodiments, the convolutional neural network 702 can be a spring network of convolutional layers. For instance, the convolutional neural network 702 can perform a plurality of sequential and/or parallel downsampling and upsampling of the image 701 associated with convolutional layers of the convolutional neural network 702 to generate, for example, a set of convolutional feature maps. In an example, the convolutional neural network 702 can perform a first convolutional layer process associated with sequential downsampling of the image 701 and a second convolutional layer process associated with sequential ups ampling of the image 701 to generate, for example, a set of convolutional feature maps. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network 702 can analyze the image 701 based on a first convolutional layer filter that comprises a first size, a second convolutional layer filter that comprises a second size that is different than the first size, and a third convolutional layer filter that comprises the first size associated with the first convolutional layer filter to generate, for example, a set of convolutional feature maps. In certain embodiments, the convolutional neural network 702 can correspond to the convolutional neural network 404.

The classification detection segmentation network 704 can be employed to classify and/or localize one or more regions of interest associated with the image 701. For example, the classification detection segmentation network 704 can receive a set of convolutional feature maps generated by the convolutional neural network 702 to facilitate classification and/or localization of one or more regions of interest associated with the image 701. In one example, the classification detection segmentation network 704 can generate a score map associated with classification and/or localization of one or more regions of interest associated with the image 701. The score map can provide, for example, a predicted classification label with a localization map. In certain embodiments, the classification detection segmentation network 704 can correspond to the convolutional neural network 408, the scoring maps 410, the decoder 411 (e.g., the upsampling 412 and/or the convolutional neural network layer 414), the global pooling 424, and/or the predicted label 426. The loss function 706 can be a loss function that is created based on a mask 708, a bounding box 714 and/or a label 720. The mask 708 can be generated, for example, during training of the convolutional neural network 702. The mask 708 can include one or more weights for one or more regions of interest in the image 701 (e.g., the image 701 provided to the convolutional neural network 702). In one example, the mask 708 can include a set of pixels that define a location for region of interests in the image 701 (e.g., the image 701 provided to the convolutional neural network 702) using binary filtering. In an embodiment, the mask 708 can correspond to the mask 416. The bounding box 714 can link one or more regions of interest to one or more class labels associated with the label 720. In one example, the bounding box 714 can link a region of interest in the image 701 (e.g., the image 701 provided to the convolutional neural network 702) to a class label associated with the label 720. In an aspect, a size of the bounding box 714 can be matched to a convolutional feature map generated by the convolutional neural network 702. For instance, the bounding box 714 can provide a location for a region of interest in the image 701 (e.g., the image 701 provided to the convolutional neural network 702) and a size of the bounding box 714 can be matched with a size of at least one convolutional feature map generated by the convolutional neural network 702. In one example, the bounding box 714 can be a predicted bounding box. In another example, the bounding box 714 can be a ground truth bounding box. In an embodiment, the bounding box 714 can correspond to the bounding box 430 and/or the bounding box prediction 432. The label 720 can be, for example, an image-level label. In an aspect, the label 720 can be a description (e.g., a textual description of a disease, etc.) associated with the image 701 (e.g., the image 701 provided to the convolutional neural network 702). For example, the label 720 can label at least a portion of the image 701 (e.g., the image 701 provided to the convolutional neural network 702) with a particular disease included in the image 701. In certain embodiments, the label 720 can label one or more regions of interest in the image 701 (e.g., the image 701 provided to the convolutional neural network 702). For example, the label 720 can label (e.g., provide a description for) a region of interest associated with the bounding box 714. In an embodiment, the label 720 can correspond to the image level labels 428 and/or the predicted label 426. In an embodiment, the loss function 706 can correspond to the fourth loss function generated by the fourth loss function component 115. For example, the loss function 706 can correspond to the loss function 502. In certain embodiments, the mask 708 can be processed by dilation 710 and/or pooling 712 prior to being received by the classification detection segmentation network 704. The dilation 710 can be, for example, a dilated pooling process. For example, the dilation 710 can be a convolution applied to the mask 708 with a set of defined gaps. The pooling 712 can be, for example, a mask pooling process that compares the mask 708 with a downsampled version of the mask 708 (e.g., a predicted mask). In certain embodiments, the bounding box 714 can be processed by fill mask 716 and/or pooling 718 prior to being received by the classification detection segmentation network 704. The fill mask 716 can be a process, for example, to fill at least a portion of the bounding box 714 with a mask. The pooling 712 can be, for example, a mask pooling process that compares the bounding box 714 with the mask 708 and/or a downsampled version of the mask 708 (e.g., a predicted mask).

Figure 8:
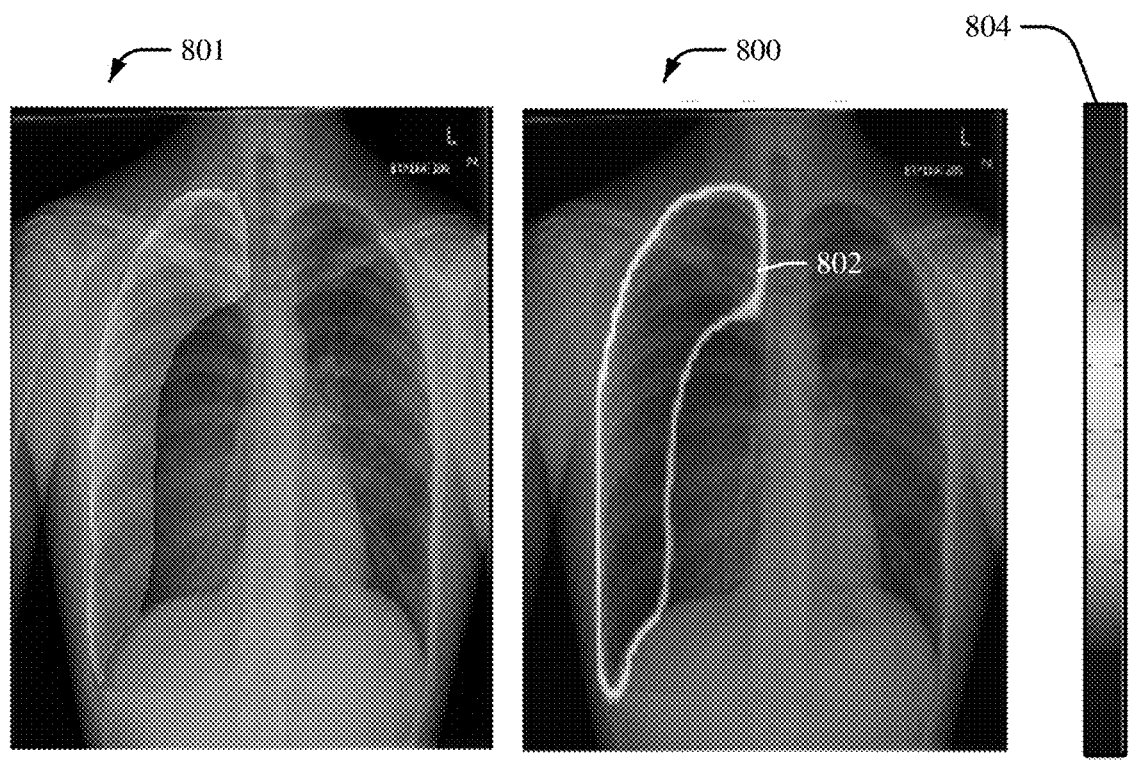
FIG. 8 illustrates another example multi-dimensional visualization, in accordance with various aspects and implementations described herein.

FIG. 8 illustrates an example multi-dimensional visualization 800 and an example input image 801, in accordance with various aspects and implementations described herein. In the embodiment shown in FIG. 8, the multi-dimensional visualization 800 can, for example, display a medical imaging diagnosis for a patient. For example, the multi-dimensional visualization 800 can display one or more classifications and/or one or more localizations for one or more conditions identified in imaging data (e.g., the input image 801). However, it is to be appreciated that the multi-dimensional visualization 800 can be associated with another type of classification and/or location for one or more features located in imaging data. In an aspect, the multi-dimensional visualization 800 can include localization data 802 for a medical imaging diagnosis. The localization data 802 can be a predicted location for a condition associated with the input image and/or the medical imaging data processed by the machine learning component 102. Visual characteristics (e.g., a color, a size, hues, shading, etc.) of the localization data 802 can be dynamic based on information provided by the machine learning component 102. For instance, a first portion of the localization data 802 can comprise a first visual characteristic, a second portion of the localization data 802 can comprise a second visual characteristic, a third portion of the localization data 802 can comprise a third visual characteristic, etc. In an embodiment, a display environment associated with the multi-dimensional visualization 800 can include a heat bar 804. The heat bar 804 can include a set of colors that correspond to different values for the localization data 802. For example, a first color (e.g., a color red) in the heat bar 804 can correspond to a first value for the localization data 802, a second color (e.g., a color green) in the heat bar 804 can correspond to a second value for the localization data 802, a third color (e.g., a color blue) in the heat bar 804 can correspond to a third value for the localization data 802, etc.

Figure 9:
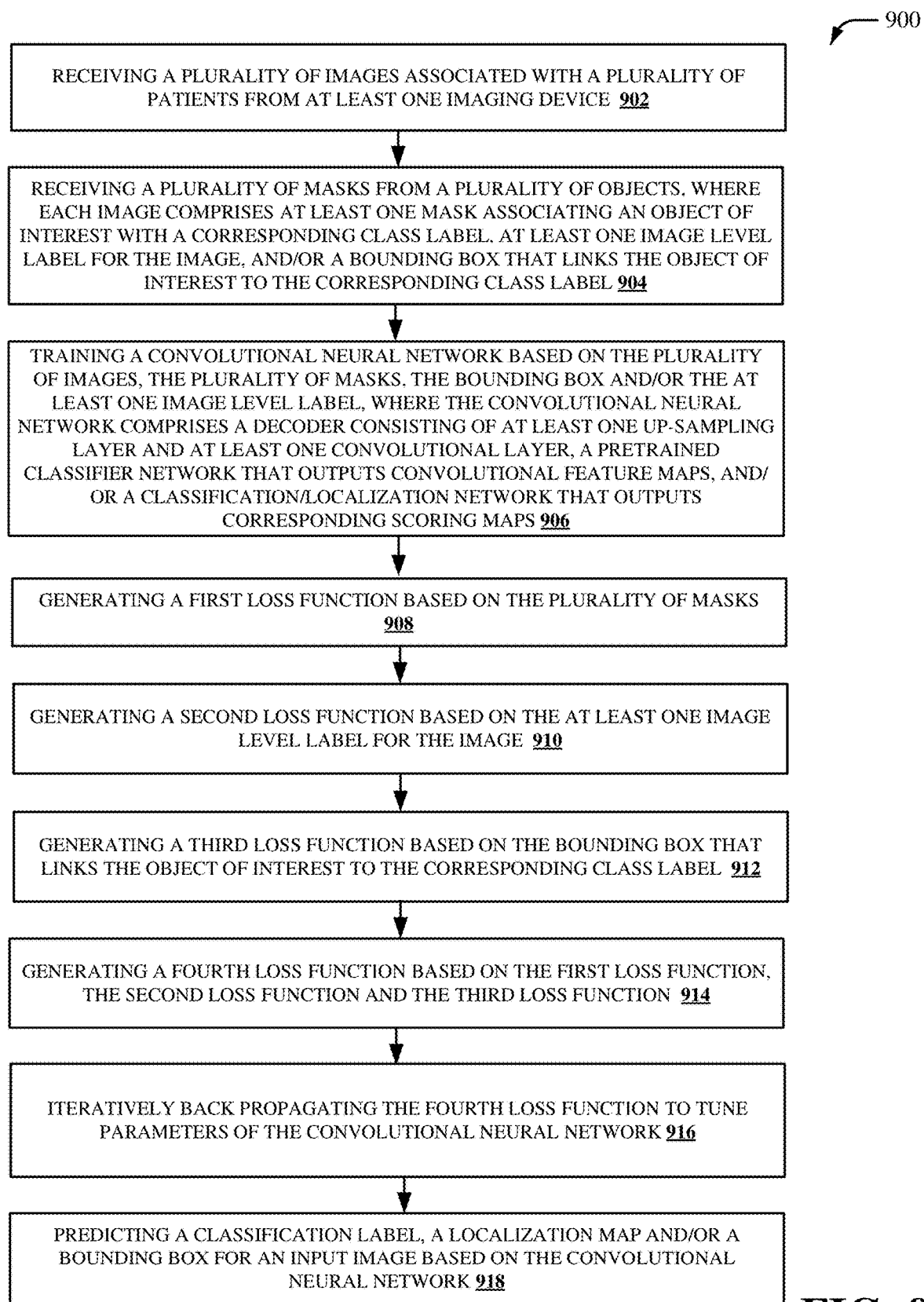
FIG. 9 depicts a flow diagram of another example method for classification and/or localization based on annotation information, in accordance with various aspects and implementations described herein.

FIG. 9 illustrates a methodology and/or a flow diagram in accordance with the disclosed subject matter. For simplicity of explanation, the methodology is depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodology in accordance with the disclosed subject matter. In addition, those skilled in the art will understand and appreciate that the methodology could alternatively be represented as a series of interrelated states via a state diagram or events. Additionally, it should be further appreciated that methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 9, there is illustrated a non-limiting implementation of a methodology 900 for classification and/or localization based on annotation information, according to an aspect of the subject innovation. At 902, a plurality of images associated with a plurality of patients is received (e.g., by training component 104) from at least one imaging device. The plurality of images can be associated with the plurality of patients. Furthermore, the plurality of images can be a set of medical images. The plurality of images can be two-dimensional images and/or three-dimensional images generated by one or more medical imaging devices. For instance, the plurality of images can be electromagnetic radiation imagery captured via a set of sensors (e.g., a set of sensors associated with a medical imaging device). In certain embodiments, the plurality of images can be a series of electromagnetic radiation imagery captured via a set of sensors (e.g., a set of sensors associated with a medical imaging device) during an interval of time. The plurality of images can be received directly from one or more medical imaging devices. Alternatively, the plurality of images can be stored in one or more databases that receives and/or stores the plurality of images associated with the one or more medical imaging devices. A medical imaging device can be, for example, an x-ray device, a CT device, another type of medical imaging device, etc. In an embodiment, each image from the plurality of images can be associated with one or more masks.

At 904, a plurality of masks from a plurality of objects is received (e.g., by training component 104), where each image comprises at least one mask associating an object of interest with a corresponding class label, at least one image level label for the image, and/or a bounding box that links the object of interest to the corresponding class label. A mask can be a filter to mask one or more regions in an image (e.g., an image from the plurality of images). For instance, a mask can include one or more weights for one or more regions of interest in an image (e.g., an image from the plurality of images). In one example, a mask can include a set of pixels that define a location for region of interests using binary filtering. The at least one image level label can be a set of labels for a set of images where each image is annotated with a label. A label can be a description (e.g., a textual description of a disease, etc.) associated with an image. For example, an image associated with the at least one image level label can be labeled with a particular disease included in the image. In an embodiment, the at least one image level label can be employed to generate a predicted label associated with the scoring maps. The predicted label can include one or more predicted classes for the scoring maps. For example, the predicted label can be a set of predicted class labels for the scoring maps. The bounding box can link one or more regions of interest to one or more class labels associated with the at least one image level label. In one example, the bounding box can link a region of interest in at least one image from the plurality of images to a class label associated with the at least one image level label. In an aspect, a size of the bounding box can be matched to a convolutional feature map generated by a convolutional neural network. In another aspect, the bounding box can provide a location for a region of interest in an image from the plurality of images. In one example, the bounding box can be a predicted bounding box. In another example, the bounding box can be a ground truth bounding box.

At 906, a convolutional neural network is trained (e.g., by training component 104) based on the plurality of images, the plurality of masks, the bounding box and/or the at least one image level label, where the convolutional neural network comprises a decoder consisting of at least one upsampling layer and at least one convolutional layer, a pretrained classifier network that outputs convolutional feature maps, and/or a classification/localization network that outputs corresponding localization maps. The decoder can be implemented as a repeatable segmentation network where the at least one upsampling layer and/or the at least one convolutional neural network layer can be repeated blocks a certain number of times.

At 908, a first loss function is generated (e.g., by first loss function component 109) based on the plurality of masks. In an aspect, the first loss function can be generated by employing the decoder to generate the localization map. In certain embodiments, a number of decoders associated with the decoder can be determined during training of the convolutional neural network. In another aspect, the first loss function can be generated based on a probability for a class associated with the plurality of masks. In an embodiment, the first loss function can be generated based on a downsampled mask (e.g., a downsampled ground truth mask) and another mask (e.g., a predicted mask) during training of the convolutional neural network. In another embodiment, the first loss function can be generated based on a downsampled mask and/or the localization map. For instance, the first loss function can be generated based on a probability for a class associated with the downsampled mask and/or a mask.

At 910, a second loss function is generated (e.g., by second loss function component 111) based on the at least one image level label associated with the plurality of images. In an aspect, the second loss function can be generated by employing the decoder to generate the localization map. In certain embodiments, a number of decoders associated with the decoder can be determined during training of the convolutional neural network. In another aspect, the second loss function can be generated based on a probability for a class associated with the at least one image level label. In an embodiment, the second loss function can be generated based on the image level labels, the predicted label and/or the localization map. For instance, the second loss function can be generated based on a probability for a class associated with the image level labels, the predicted label and/or the localization map.

At 912, a third loss function is generated (e.g., by third loss function component 113) based on the bounding box that links the object of interest to the corresponding class label. The object of interest can be, for example a region of interest in an image. In an aspect, the third loss function can be generated by employing the decoder to generate the localization map. In certain embodiments, a number of decoders associated with the decoder can be determined during training of the convolutional neural network. In another aspect, the third loss function can be generated based on a probability for a class associated with the bounding box.

At 914, a fourth loss function is generated (e.g., by fourth loss function component 115) based on the first loss function, the second loss function and the third loss function. For instance, a first weight can be applied to the first loss function, a second weight can be applied to the second loss function, and a third weight can be applied to the third loss function. Additionally, the first loss function, the second loss function and the third loss function can be combined (e.g., the first loss function, the second loss function and the third loss function can be added together). In one example, the second weight can be different than the first weight and/or the third weight. In another example, the second weight can correspond to the first weight and/or the third weight.

At 916, the fourth loss function is iteratively back propagated (e.g., by third loss function component 113) to tune parameters of the convolutional neural network based on the training data. For example, the fourth loss function can be provided to the at least one convolutional neural network layer for the decoder. Additionally, the fourth loss function can be back propagated from the at least one convolutional neural network layer to the convolutional neural network to modify one or more portions of the convolutional neural network.

At 918, a classification label, a localization map and/or a bounding box for an input image is predicted (e.g., by classification component 108) based on the convolutional neural network. The convolutional neural network employed to predict the classification label can be a version of the convolutional neural that is tuned based on the fourth loss function. The image can be, for example, a medical image. The input image can be a two-dimensional image (e.g., a two-dimensional medical image) and/or three-dimensional image (e.g., a three-dimensional medical image) generated by one or more medical imaging devices. For instance, the input image can be a two-dimensional image (e.g., a two-dimensional medical image) and/or three-dimensional image (e.g., a three-dimensional medical image) generated by an x-ray device, a CT device, another type of medical imaging device, etc. In one example, the input image can be an electromagnetic radiation image captured via a set of sensors (e.g., a set of sensors associated with a medical imaging device). In certain embodiments, the input image can be a series of electromagnetic radiation images captured via a set of sensors (e.g., a set of sensors associated with a medical imaging device) during an interval of time. The input image can be received directly from one or more medical imaging devices. Alternatively, the input image can be stored in one or more databases that receives and/or stores the input image associated with the one or more medical imaging devices. The localization map for the input image can include, for example, information representing a probability score for one or more regions of the input image. In an embodiment, the localization map for the input image can include a visualization representing a probability score for one or more regions of the input image. The bounding box for the input image can be a predicted bounding box that links one or more regions of interest in the input image to one or more class labels associated with the input image. In an aspect, the bounding box for the input image can provide a location for a region of interest in the input image. In certain embodiments, the methodology 900 can further include matching a size of a mask from the plurality of masks with a size of a convolutional feature map from the convolutional feature maps. In certain embodiments, the methodology 900 can further include matching a size of a mask from the plurality of masks with a size of a convolutional feature map from the convolutional feature maps based on a mask pooling process. In certain embodiments, the methodology 900 can further include generating a multi-dimensional visualization associated with the classification label for the input image. In certain embodiments, the decoder can generate a localization map. For instance, the decoder can perform a decoding process associated with the at least one upsampling layer and/or the at least one convolutional neural network layer to generate a localization map.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 10:
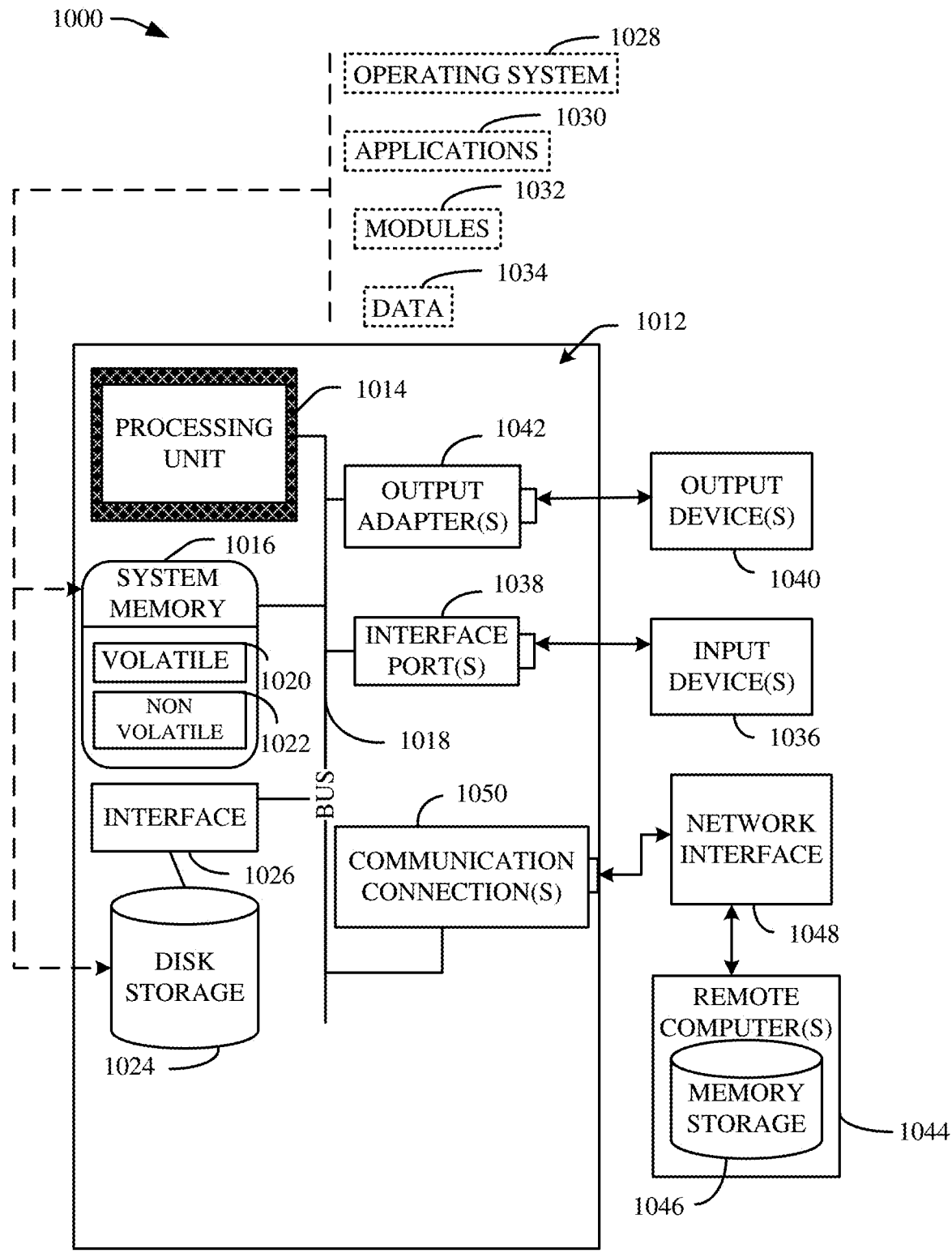
FIG. 10 is a schematic block diagram illustrating a suitable operating environment.
Figure 11:
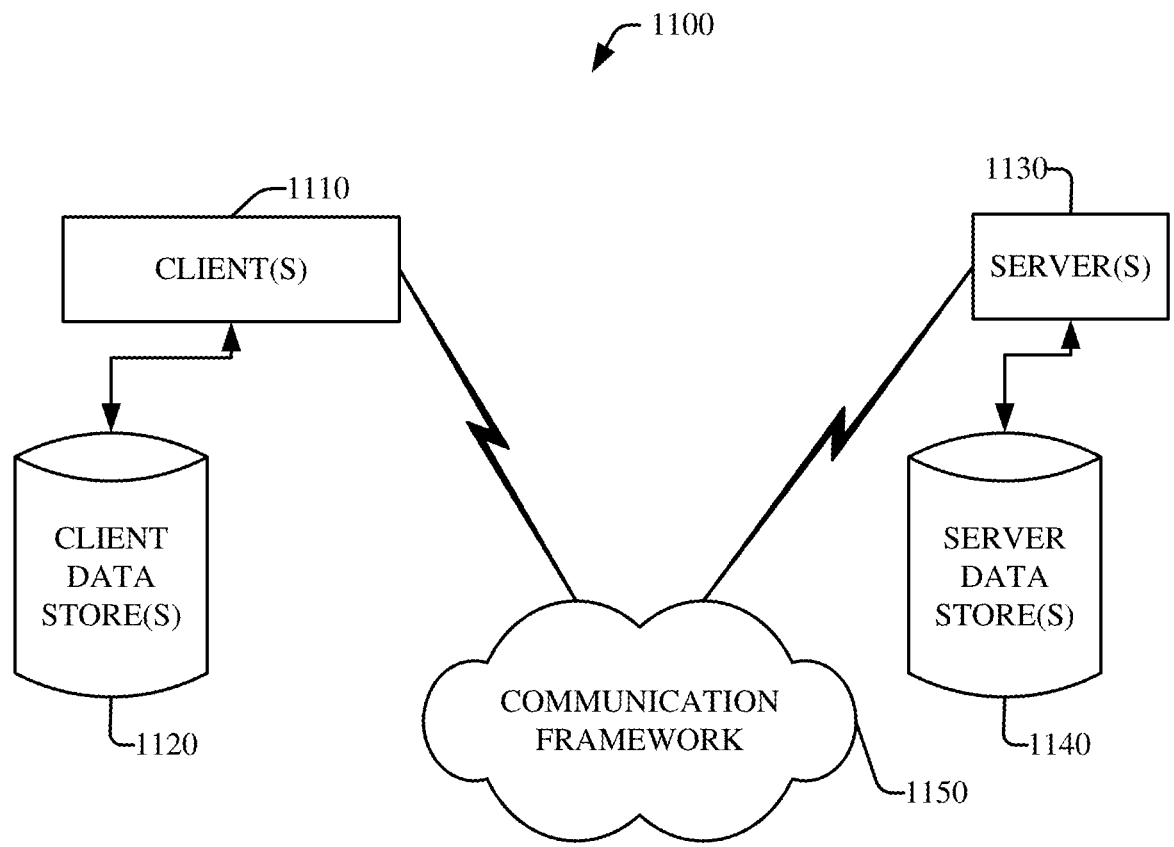
FIG. 11 is a schematic block diagram of a sample-computing environment.

In order to provide a context for the various aspects of the disclosed subject matter, FIGS. 10 and 11 as well as the following discussion are intended to provide a brief, general description of a suitable environment in which the various aspects of the disclosed subject matter may be implemented.

With reference to FIG. 10, a suitable environment 1000 for implementing various aspects of this disclosure includes a computer 1012. The computer 1012 includes a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014.

The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1016 includes volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 also includes removable/non-removable, volatile/non-volatile computer storage media. FIG. 10 illustrates, for example, a disk storage 1024. Disk storage 1024 includes, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1024 to the system bus 1018, a removable or non-removable interface is typically used, such as interface 1026.

FIG. 10 also depicts software that acts as an intermediary between users and the basic computer resources described in the suitable operating environment 1000. Such software includes, for example, an operating system 1028. Operating system 1028, which can be stored on disk storage 1024, acts to control and allocate resources of the computer system 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems.

A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port may be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a personal computer, a server, a router, a network PC, a workstation, a microprocessor based appliance, a peer device or other common network node and the like, and typically includes many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1050 refers to the hardware/software employed to connect the network interface 1048 to the bus 1018. While communication connection 1050 is shown for illustrative clarity inside computer 1012, it can also be external to computer 1012. The hardware/software necessary for connection to the network interface 1048 includes, for exemplary purposes only, internal and external technologies such as, modems including regular telephone grade modems, cable modems and DSL modems, ISDN adapters, and Ethernet cards.

FIG. 11 is a schematic block diagram of a sample-computing environment 1100 with which the subject matter of this disclosure can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing this disclosure, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. The client(s) 1110 are operatively connected to one or more client data store(s) 1120 that can be employed to store information local to the client(s) 1110. Similarly, the server(s) 1130 are operatively connected to one or more server data store(s) 1140 that can be employed to store information local to the servers 1130.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A machine learning system, comprising:
   a memory that stores computer executable components;
   a processor that executes the computer executable components stored in the memory, wherein the computer executable components comprise:
     a training component that trains a convolutional neural network based on training data associated with a plurality of patients and a plurality of images, wherein the training data is received from at least one imaging device, wherein respective images of the plurality of images are associated with a plurality of masks, a plurality of image level labels, and a bounding box that links a region of interest to a class label and comprises a set of coordinates for a location of the region of interest within the respective images;
     a first loss function component that generates a first loss function based on the plurality of masks;
     a second loss function component that generates a second loss function based on the plurality of image level labels for the plurality of images;
     a third loss function component that generates a third loss function based on the bounding box that links the region of interest to the class label;
     a fourth loss function component that generates a fourth loss function based on the first loss function, the second loss function and the third loss function, wherein the fourth loss function is iteratively back propagated to tune parameters of the convolutional neural network; and
     a classification component that predicts a classification label for an input image based on the convolutional neural network.

2. The machine learning system of claim 1, wherein the convolutional neural network comprises a pretrained classifier network that outputs convolutional feature maps.

3. The machine learning system of claim 2, wherein the convolutional neural network comprises a classification/localization network that outputs corresponding localization maps based on the convolutional feature maps.

4. The machine learning system of claim 2, wherein a first size of the bounding box is matched with a second size of a convolutional feature map from the convolutional feature maps.

5. The machine learning system of claim 2, wherein a first size of a mask from the plurality of masks is matched with a second size of a convolutional feature map from the convolutional feature maps based on a mask pooling process.

6. The machine learning system of claim 1, wherein the first loss function component generates the first loss function based on a probability for a class associated with the plurality of masks.

7. The machine learning system of claim 1, wherein the second loss function component generates the second loss function based on a probability for a class associated with the plurality of image level labels.

8. The machine learning system of claim 1, wherein the fourth loss function component applies a first weight to the first loss function, applies a second weight to the second loss function, and applies a third weight to the third loss function.

9. The machine learning system of claim 1, wherein the computer executable components further comprise:
   a visualization component that generates a multi-dimensional visualization associated with the classification label for the input image.

10. A method, comprising using a processor operatively coupled to memory to execute computer executable components to perform the following acts:
   receiving, from at least one imaging device, a plurality of images associated with a plurality of patients;
   receiving a plurality of masks, wherein respective images of the plurality of images comprises at least one mask of the plurality of masks, wherein the at least one mask associates an object of interest with a corresponding class label, at least one image level label for the respective images, and a bounding box that links the object of interest to the corresponding class label, wherein the least one image level label comprises a description of a region of interest, and wherein the bounding box comprises a height value and a width value for a location associated with the region of interest;

training a convolutional neural network based on the plurality of images, the plurality of masks, the bounding box, and the at least one image level label, wherein the convolutional neural network comprises a pre-trained classifier network that outputs convolutional feature maps, and a classification/localization network that outputs corresponding localization maps;

generating a first loss function based on the plurality of masks;

generating a second loss function based on the at least one image level label for the respective images;

generating a third loss function based on the bounding box that links the object of interest to the corresponding class label;

generating a fourth loss function based on the first loss function, the second loss function and the third loss function;

iteratively back propagating the fourth loss function to tune parameters of the convolutional neural network; and predicting a classification label for an input image based on the convolutional neural network.

11. The method of claim 10, further comprising matching a first size of the bounding box with a second size of a convolutional feature map from the convolutional feature maps.

12. The method of claim 10, further comprising matching a first size of a mask from the plurality of masks with a second size of a convolutional feature map from the convolutional feature maps based on a mask pooling process.

13. The method of claim 10, wherein the generating the first loss function comprises generating the first loss function based on a probability for a class associated with the plurality of masks.

14. The method of claim 10, wherein the generating the second loss function comprises generating the second loss function based on a probability for a class associated with the at least one image level label.

15. The method of claim 10, wherein the generating the fourth loss function comprises applying a first weight to the first loss function, applying a second weight to the second loss function, and applying a third weight to the third loss function.

16. The method of claim 10, further comprising generating a multi-dimensional visualization associated with the classification label for the input image.

17. A computer readable storage device comprising instructions that, in response to execution, cause a system comprising a processor to perform operations, the operations comprising:

receiving, from at least one imaging device, a plurality of images associated with a plurality of patients;

receiving a plurality of masks, wherein respective images of the plurality of images comprise at least one mask of the plurality of masks, wherein the at least one mask associates an object of interest with a corresponding class label, at least one image level label for the respective image, and a bounding box that links the object of interest to the corresponding class label, and wherein the bounding box comprises a set of coordinates that provide an indication of a location, within the respective images, for a region of interest;

training a convolutional neural network based on the plurality of images, the plurality of masks, the bounding box, and the at least one image level label, wherein the convolutional neural network comprises a pre-trained classifier network that outputs convolutional feature maps, and a classification/localization network that outputs corresponding localization maps;

generating a first loss function based on the plurality of masks;

generating a second loss function based on the at least one image level label for the image;

generating a third loss function based on the bounding box that links the object of interest to the corresponding class label;

generating a fourth loss function based on the first loss function, the second loss function and the third loss function;

iteratively back propagating the fourth loss function to tune parameters of the convolutional neural network; and predicting a classification label for an input image based on the convolutional neural network.

18. The computer readable storage device of claim 17, wherein the generating the first loss function comprises generating the first loss function based on a probability for a class associated with the plurality of masks.

19. The computer readable storage device of claim 17, wherein the generating the second loss function comprises generating the second loss function based on a probability for a class associated with the at least one image level label.

20. The computer readable storage device of claim 17, wherein the operations further comprise generating a multi-dimensional visualization associated with the classification label for the input image.

* * * * *